United States Patent
Takeuchi et al.

(10) Patent No.: US 7,656,514 B2
(45) Date of Patent: Feb. 2, 2010

(54) METHOD AND APPARATUS FOR EVALUATING SEMICONDUCTOR LAYERS

(75) Inventors: Hideo Takeuchi, Tokyo (JP);
Yoshitsugu Yamamoto, Tokyo (JP)

(73) Assignee: Mitsubishi Electric Corporation, Tokyo (JP)

( * ) Notice: Subject to any disclaimer, the term of this patent is extended or adjusted under 35 U.S.C. 154(b) by 567 days.

(21) Appl. No.: 11/486,271

(22) Filed: Jul. 14, 2006

(65) Prior Publication Data
US 2007/0026594 A1    Feb. 1, 2007

(30) Foreign Application Priority Data
Jul. 28, 2005  (JP) .............................. 2005-218329

(51) Int. Cl.
*G01N 21/00*   (2006.01)
(52) U.S. Cl. .................... 356/237.1; 356/445
(58) Field of Classification Search ... 356/237.1–237.5, 356/445
See application file for complete search history.

(56) References Cited

U.S. PATENT DOCUMENTS

| | | | |
|---|---|---|---|
| 4,953,983 A | * | 9/1990 | Bottka et al. ................ 356/445 |
| 5,796,484 A | * | 8/1998 | Honma et al. ............... 356/600 |
| 6,762,831 B2 | * | 7/2004 | Shibata et al. ............ 356/237.2 |

FOREIGN PATENT DOCUMENTS

| | | |
|---|---|---|
| JP | 2-307046 | 12/1990 |
| JP | 7-92236 | 4/1995 |
| JP | 2003-224171 | 8/2003 |

OTHER PUBLICATIONS

Shen, H.; "Franz-Keidysh oscillations in modulation spectroscopy", J. *Applied Physics*, vol. 78, No. 4, pp. 2151-2176 (Aug. 15, 1995).

* cited by examiner

*Primary Examiner*—L. G Lauchman
(74) *Attorney, Agent, or Firm*—Leydig, Voit & Mayer, Ltd.

(57) ABSTRACT

A method for evaluating semiconductor layers includes irradiating semiconductor layers on a substrate with light; measuring an optical spectrum peculiar to excitons in the semiconductor layers; and analyzing a broadening factor of optical spectral features of the optical spectrum. The method provides a quick measurement of a surface state of the semiconductor layers with high accuracy.

8 Claims, 22 Drawing Sheets

METHOD AND APPARATUS FOR EVALUATING SEMICONDUCTOR LAYERS

BACKGROUND OF THE INVENTION

1. Field of the Invention

The present invention relates to a method and an apparatus for evaluating semiconductor layers formed on a substrate.

2. Description of the Related Art

In general, a nitride semiconductor, which is a generic term of mixed crystals expressed by a composition formula: $Al_xIn_yGa_{1-x-y}N$ ($0 \leq x \leq 1$, $0 \leq y \leq 1$, $x+y<1$), such as gallium nitride (GaN), aluminum nitride (AlN), indium nitride (InN), is mechanically robust and chemically stable. In addition, the nitride semiconductors exhibit high thermal conductivity and excellent heat dissipation. Semiconductor devices composed of the nitride semiconductors, for example, HEMTs (high electron mobility transistors) composed of AlGaN/GaN layers and LDs (laser diodes) composed of InGaN/GaN layers, are suitable for high power operations.

Meanwhile, the nitride semiconductors have a remarkably high melting point. For example, AlN has a melting point of 3,273 K (Kelvin), GaN 2,000 K or more, and InN 1,373 K, respectively (document: S. Sakai, "III-nitride semiconductor", edited by I. Akazaki, Chapter 1, published by Baifukan CO., LTD, 1999). Hence it is relatively difficult to grow nitride semiconductor layers with high crystallinity. In fact, it is known that cracks of the order of nanometers may be formed on a surface of the nitride semiconductor layer, depending on slight variations of growth condition. These cracks may increase gate leak current and degrade pulse response characteristics in HEMT devices. Accordingly, quantitative evaluation of crack density is quite important in manufacturing nitride semiconductor devices.

Conventional quantitative evaluation of a surface state, such as crack density, was performed mainly using AFM (atomic force microscope). The AFM can measure displacement of a cantilever by detecting reflected light from the cantilever when the cantilever is displaced based on atomic force between a probe fixed onto the tip of the cantilever and atoms on the surface of a sample. The cantilever or the sample is scanned and moved vertically so as to keep the displacement of the probe constant, in which conversion of the control signal into an image enables the surface state (concavity and convexity) of the sample to be measured at the atomic order.

The AFM has an advantage of directly evaluating the surface state, whereas it has a disadvantage of a low throughput in data acquisition. In addition, the AFM is also remarkably expensive and unsuitable for applying to mass production lines.

For another approach of directly evaluating a surface state, STM (scanning tunneling microscope) or KFM (Kelvin force microscope) is known but has the same problem as the AFM does.

Therefore, desired is a method for measuring a surface state quickly and sensitively with a relatively simple constitution.

Cracks existing in a semiconductor layer give a great influence on crystallinity of a surface. Hence by measuring parameters relatively sensitive to crystallinity among physical parameters of the semiconductor layer, the surface state of the semiconductor layer can be evaluated indirectly.

One parameter typically used among the parameters sensitive to crystallinity is a band width at half maximun of an X-ray diffraction pattern. The band width at half maximun is increased as crystallinity of the semiconductor layer is degraded; therefore it is relatively easy to measure. Thus, this parameter is often utilized for evaluating crystallinity of bulk crystals.

However, since the X-ray diffraction pattern is influenced not only by the surface of the crystal but also by an internal state thereof, a change of the band width at half maximun is strongly dominated by a change in the internal state of the crystal, consequently, not so sensitive to a change in the surface state of the crystal.

The band width at half maximun of the X-ray diffraction pattern, as described above, exhibits a physical value depending on the change in the surface state of the crystal as well as the surface of the crystal, hence, unsuitable for evaluating only the surface state of the crystal. Further, in case of a plurality of semiconductor layers, each having a different composition, being stacked on a substrate, the X-ray diffraction pattern may be influenced both by crystalline states of all the semiconductor layers and by a crystalline state of the substrate, thereby hardly separating only information regarding a particular semiconductor layer.

The related prior arts are listed as follows: Japanese Patent Unexamined Publications (kokai) JP-A-2-307046 (1990), JP-A-7-92236 (1995), and JP-A-2003-224171 (2003).

SUMMARY OF THE INVENTION

An object of the present invention is to provide a method and an apparatus for evaluating semiconductor layers, which can quickly measure a surface state of the semiconductor layer with high accuracy.

A method for evaluating semiconductor layers, according to an aspect of the present invention, includes steps of: irradiating with light semiconductor layers on a substrate; measuring an optical spectrum peculiar to excitons in the semiconductor layers; and analyzing a broadening factor of the spectral features.

It is preferable in the present invention that the broadening factor is quantified by expressing a refractive index function of any surface state using a calculation model of convolution of both a refractive index function peculiar to a material and a distribution function.

Further, it is preferable in the present invention that the semiconductor layers under test are formed of nitride semiconductors.

An apparatus for evaluating semiconductor layers, according to another aspect of the present invention, includes: a sample stage for holding a sample having semiconductor layers under test; a light source for irradiating the semiconductor layers with light; a spectrum measuring apparatus for measuring an optical spectrum peculiar to excitons; and a spectrum analyzing apparatus for analyzing a broadening factor of the optical spectral features.

It is preferable in the present invention that the apparatus further includes: an optical path detection apparatus for detecting a deviation of the optical path of the light reflected from the sample; and an adjusting mechanism for adjusting the position or the angle of the sample stage based on the deviation of the optical path detected by the optical path detection apparatus.

Moreover, it is preferable in the present invention that the apparatus further includes: a splitting optical device for picking up a part of the light reflected from the sample S; and an optical position detector for detecting a position of light picked up by the splitting optical device.

A method for evaluating semiconductor layers, according to yet another aspect of the present invention, includes: irradiating with light semiconductor layers on a substrate; applying modulation of a predetermined frequency to the semiconductor layers so as to change physical characteristics of the semiconductor layers; detecting the light reflected from the semiconductor layers; extracting a component of the modulation frequency out of the detected signal of the reflected light; and measuring an optical spectrum peculiar to excitons while changing wavelength of the irradiating light.

It is preferable in the present invention that, in the modulation applying step, the semiconductor layers are irradiated with excitation light modulation at the predetermined frequency.

Further, it is preferable in the present invention that, in the modulation applying step, the semiconductor layers are applied with an electric field modulation at the predetermined frequency.

Furthermore, it is preferable in the present invention that, in the modulation applying step, the semiconductor layers are applied with a stress modulated at the predetermined frequency.

According to the present invention, an optical spectrum peculiar to excitons is measured. In a case where the crystalline defects such as crack little exist, a sharp spectrum of excitons can be obtained. In another case of more crystalline defects, a broad spectrum of excitons can be obtained. Therefore, a surface state of the semiconductor layers can be evaluated by analyzing a broadening factor of the spectrum of excitons.

Accordingly, the present invention, in which an optical spectrum analysis method is employed, has a higher throughput in data acquisition in comparison to the conventional AFM observation method and X-ray diffraction pattern method. The evaluation apparatus has a relatively simple constitution and can be easily introduced to mass production lines.

DETAILED DESCRIPTION OF THE PREFERRED EMBODIMENTS

This application is based on an application No. 2005-218329 filed Jul. 28, 2005 in Japan, the disclosure of which is incorporated herein by reference.

Hereinafter, preferred embodiments will be described with reference to drawings.

Embodiment 1

Figure 1:
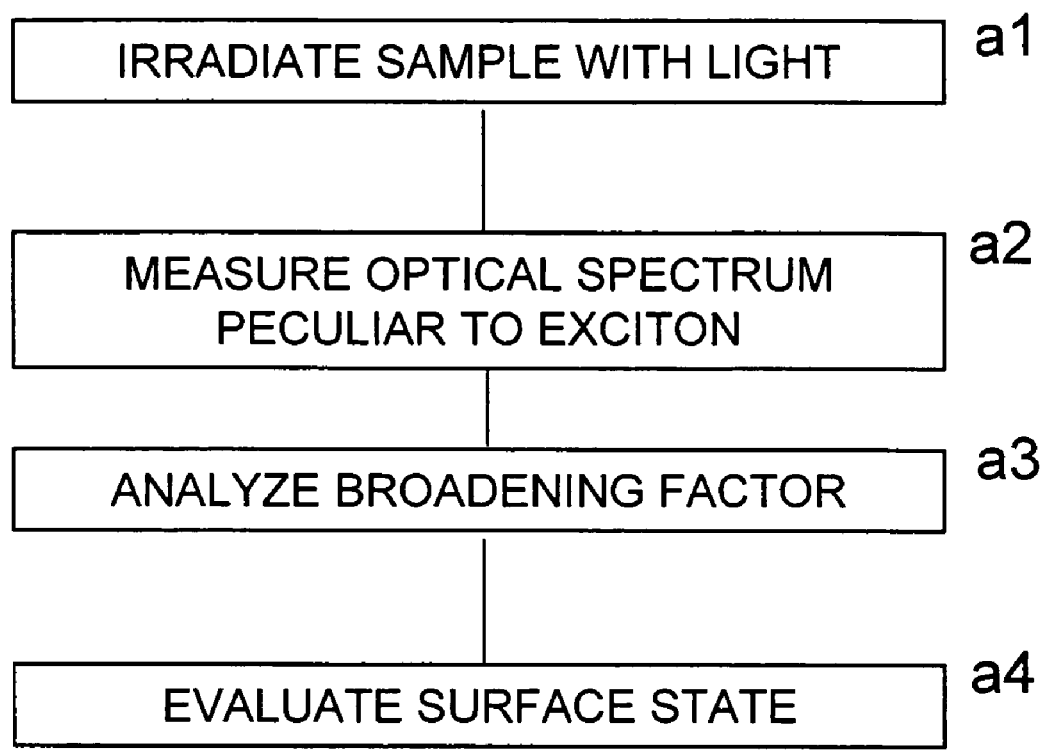
FIG. 1 is a flow chart showing an example of a method for evaluating a surface, according to the present invention.
Figure 2:
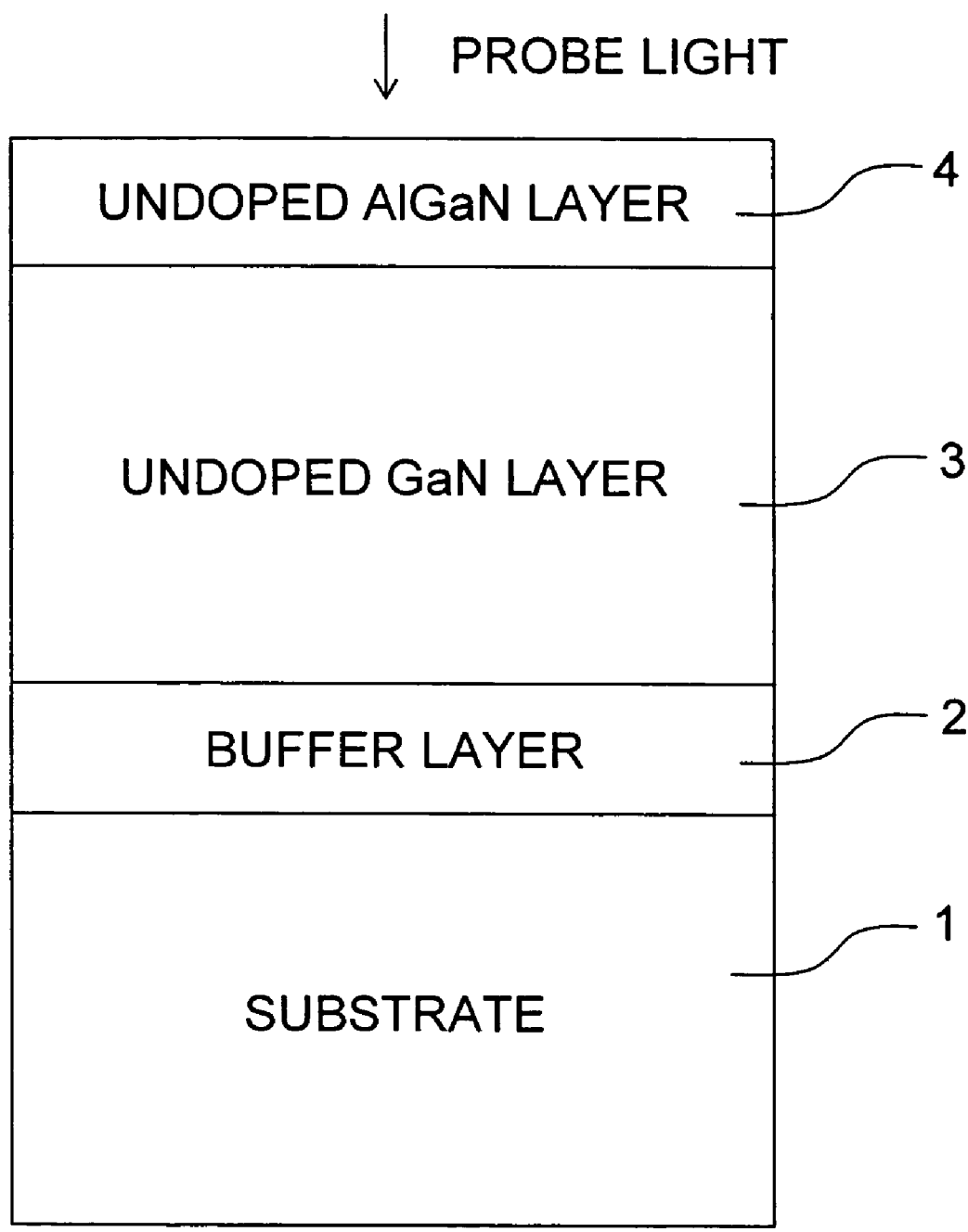
FIG. 2 is a cross-sectional view showing a typical sample.

FIG. 1 shows a flow chart of a method for evaluating a surface, according to the present invention. Herein exemplified is, for a typical sample, a nitride semiconductor epitaxial wafer which has a HEMT (high electron mobility transistor) structure consisting of buffer layer 2, undoped GaN layer 3 and undoped AlGaN layer 4 are sequentially grown on substrate 1, as shown in FIG. 2.

First, in step a1 of FIG. 1, the surface of the undoped AlGaN layer 4, which is located at an uppermost layer of the sample, is irradiated with probe light. Next, in step a2, an optical reflection spectrum peculiar to an exciton in the undoped AlGaN layer 4 is measured.

For a method of measuring the reflection spectrum, a) monochromatic light is used for the probe light, and then a change of intensity of reflected light from the sample is measured while changing the wavelength of the probe light, or b) continuous spectrum light is used for the probe light, and then the reflection spectrum of reflected light from the sample is measured using a spectroscope.

The resultant reflectance will be calibrated as follows: primarily, intensity of the reflected light $I_{ref}(\lambda)$ with respect to wavelength $\lambda$ is measured using a reference sample having a known reflectance $R_{ref}(\lambda)$, for example, a metal-coated mirror. Next, intensity of the reflected light $I_{sample}(\lambda)$ is measured using the sample. Next, by using a definition: reflectance=(intensity of light reflected on the surface of the sample)/(intensity of light incident onto the surface of the sample), the intensity of light incident onto the surface of the sample is given by $I_{ref}(\lambda)/R_{ref}(\lambda)$. Therefore, the reflectance $R_{sample}(\lambda)$ of the sample can be expressed by the following equation (1).

$$R_{sample}(\lambda) = \frac{R_{ref}(\lambda) \cdot I_{sample}(\lambda)}{I_{ref}(\lambda)} \quad (1)$$

where $R_{ref}(\lambda)$ is a known value, and $I_{ref}(\lambda)$ and $I_{sample}(\lambda)$ can be obtained by measurement. Hence, the reflectance $R_{sample}(\lambda)$ of the sample can be obtained by calculation using a computer or the like.

Next, in step a3 of FIG. 1, a broadening factor of the reflectance spectrum $R_{sample}(\lambda)$ of the sample is analyzed.

Incidentally, the exciton, which is a kind of a pair of electron and hole generated in electrically insulating materials or semiconductor materials, in particular, is known to exist stably in nitride semiconductors at room temperature. The exciton is a kind of elementary excitation in a solid substance, and exhibits a characteristic structure in an optical spectrum around photon energy corresponding to the energy thereof. In the case where irregularities exist on the surface of a sample, the spectrum peculiar to the exciton tends to be broader. Consequently, the spectral width can be quantified by a broadening factor.

Assuming that the irregularities of the sample obey a Gaussian distribution, the refractive index $n_{AlGaN}(\lambda)$ of the undoped AlGaN layer 4 can be phenomenologically defined by the following equation (2).

$$n_{AlGaN}(\lambda) \equiv \frac{\int n_{AlGaN}(\lambda') \cdot \exp(-(\lambda' - \lambda)^2 / 2\sigma^2) d\lambda'}{\int \exp(-(\lambda' - \lambda)^2 / 2\sigma^2) d\lambda'} \quad (2)$$

The equation (2) expresses a refractive index function of any surface state using a calculation model of convolution of both a refractive index function peculiar to a material (herein $n_{AlGaN}(\lambda)$) and a distribution function (herein Gaussian distribution). In this calculation model, a standard deviation a of the Gaussian distribution is a parameter corresponding to the broadening factor.

Next, when the refractive index $n(\lambda)$ of the sample is given, the reflectance spectrum $R(\lambda)$ can be easily obtained using various calculation models for reflection spectrum, such as transfer matrix method. For a simple example, in a case where the undoped GaN layer 3 is sufficiently thick to take account of interference effect only in the undoped AlGaN layer 4, the reflectance spectrum around exciton energy in the undoped AlGaN layer 4 can be given by the following equation (3).

$$R(\lambda) = \left| \frac{n_{Air} - n_{AlGaN}}{n_{Air} + n_{AlGaN}} + \frac{4 e^{2i\delta} n_{Air} n_{AlGaN} (n_{AlGaN} - n_{GaN})}{(n_{Air} + n_{AlGaN})^2 (n_{AlGaN} + n_{GaN})} \right|^2 \quad (3)$$

where $n_{Air}$ and $n_{GaN}$ are refractive indices of air and GaN, respectively. The physical value δ denotes a difference in phase between two kinds of light causing interference, that is, one light reflected on the uppermost surface of the undoped AlGaN layer 4 and another light reflected by the interface of AlGaN/GaN, which is given by the following equation (4).

$$\delta = \frac{4\pi \cdot n_{AlGaN}}{\lambda} \cdot d_{AlGaN} \cdot \cos\theta_{ref} \quad (4)$$

Accordingly, the broadening factor can be extracted by analyzing the reflection spectrum using the above-described equation (2) and the known equations (3) and (4).

Next, in step a4 of FIG. 1, the surface state of the undoped AlGaN layer 4 is evaluated based on the extracted broadening factor. In the calculation model of the equation (2), the broader exciton spectral structure can exhibit the larger standard deviation σ as the broadening factor, thereby judging that the surface state of the undoped AlGaN layer 4 is inferior. In contrast, the sharper exciton spectrum can exhibit the smaller standard deviation σ as the broadening factor, thereby judging that the surface state of the undoped AlGaN layer 4 is superior.

Figure 3:
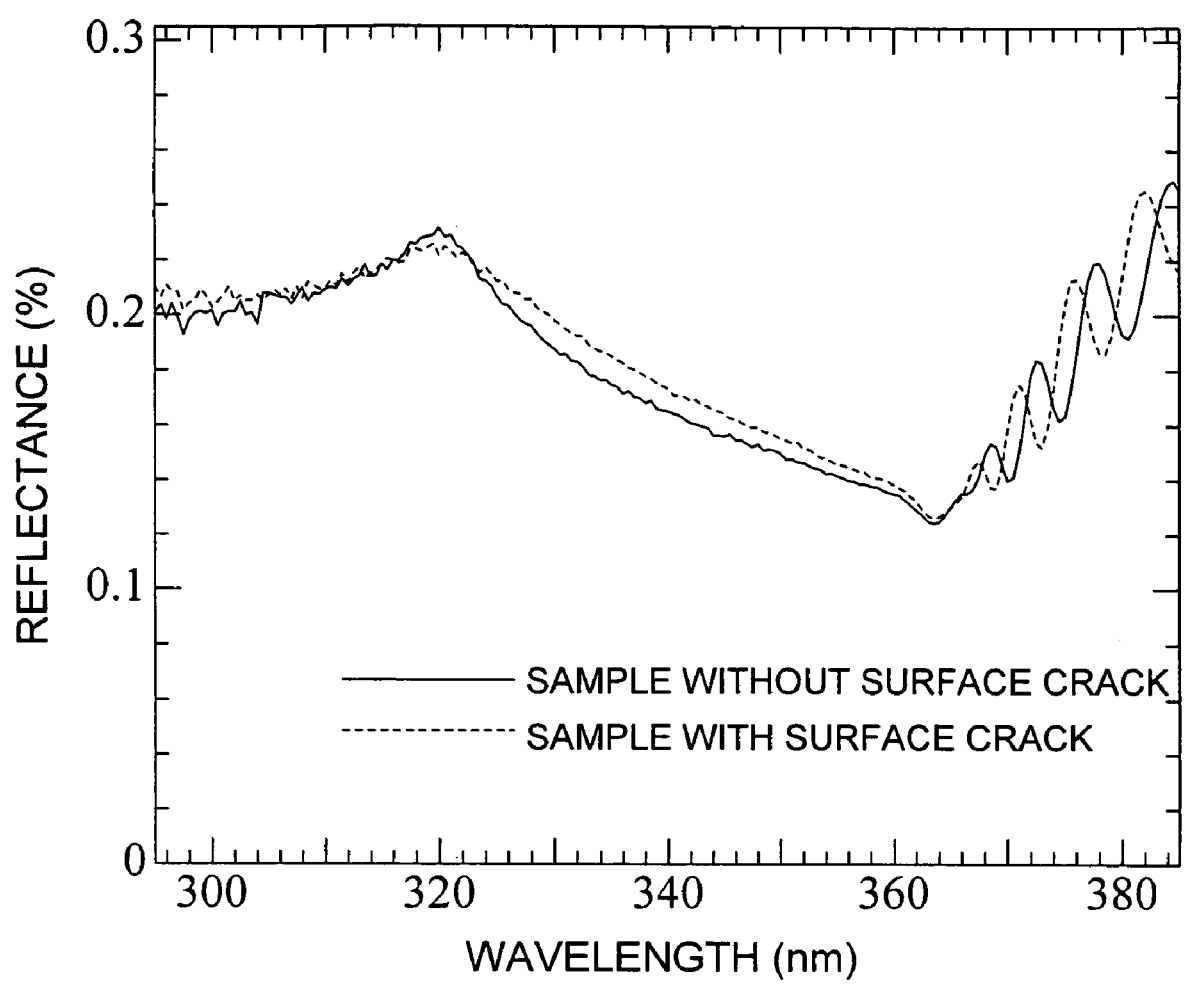
FIG. 3 is a graph showing an example of reflectance spectra of nitride semiconductors.

FIG. 3 shows an example of reflectance spectra of nitride semiconductors. The vertical axis corresponds to reflectance (%), and the horizontal axis corresponds to wavelength (nm). The solid line shows a sample having no crack on the surface, and the dashed line shows another sample having a crack on the surface.

The center of the exciton spectral feature is located around 320 nm. The spectrum of the dashed curve is broader than the spectrum of the solid curve. The broadening factor of each spectrum can be numerically calculated by a computer using the above-mentioned equations (2) to (4). Therefore, by using the resultant broadening factor, the surface state of the sample can be evaluated quantitatively.

As described above, a nitride semiconductor HEMT device is exemplified for the sample. The present invention can be applied to various semiconductor wafers, e.g., Si, GaAs, for transistor devices, light emitting devices and light detecting devices. In this case, appropriate wavelength of irradiating light depending on an exciton energy peculiar to the material should be chosen.

The present invention is suitable to use a sample including a nitride semiconductor, which is a generic term of mixed crystals expressed by a composition formula: $Al_x In_y Ga_{1-x-y} N$ ($0 \leq x \leq 1$, $0 \leq y \leq 1$, $x+y<1$), such as gallium nitride (GaN), aluminum nitride (AlN), indium nitride (InN), since the nitride semiconductor has a larger band gap energy, in which exciton can exist stably at room temperature, thereby resulting in a sharper exciton spectrum and evaluating the surface state with higher is precision.

Further, in this embodiment, an exciton spectral feature of a sample is measured using a reflection-type optical system. In a case where the sample is sufficiently thinner as compared to a penetration length of the probe light and the substrate is transparent for the probe light, an exciton spectral feature can be measured using a transmission-type optical system.

Embodiment 2

Figure 4:
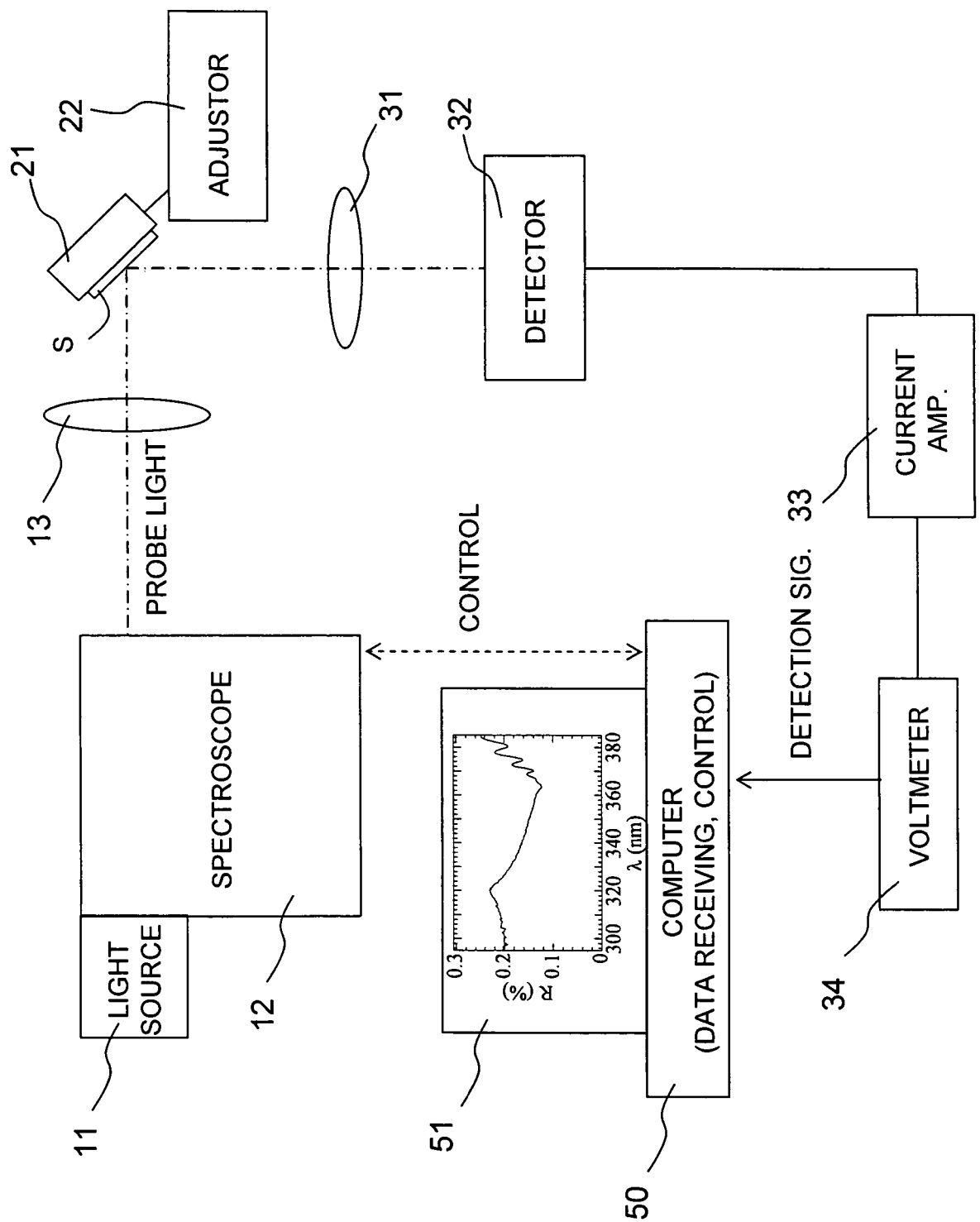
FIG. 4 is a block diagram showing an example of an surface evaluating apparatus according to the present invention.

FIG. 4 is a block diagram showing an example of an surface evaluating apparatus according to the present invention. The surface evaluating apparatus includes light source 11, spectroscope 12, sample stage 21, detector 2, and computer 50.

The light source 11 generates light with the continuous spectrum that covers a wavelength range required for spectrum measurement. The spectroscope 12 disperses the light with the continuous spectrum from the light source 11 to output monochromatic probe light. The wavelength of the probe light can be changed continuously according to a control signal from the computer 50. The probe light from the spectroscope 12 is focused onto the measurement area of the sample S with a desired spot size.

The sample stage 21 holds the sample S so as to adjust the three-dimensional position (X-Y-Z directions) or angles (pitch, yaw and roll) of the sample S using adjusting mechanism 22. The adjusting mechanism 22 may be manually operated or be operated according to a control signal from the computer 50.

The light reflected from the sample S is collected into the detector 32 by condenser lens 31. The detector 32 operates as to convert intensity of light into an electronic signal. The current signal from the detector 32 is converted into a voltage signal by subsequent current amplifier 33, and then into a digitized detection signal by a subsequent voltmeter 34.

The computer 50 receives the detection signal from the voltmeter 34 to store it in a memory or the like, and if needed, indicate the data on display 51.

This surface evaluating apparatus can operate based on the flow chart shown in FIG. 1. First, the sample S, for example, the nitride semiconductor wafer as shown in FIG. 2, is attached onto the sample stage 21. Next, the computer 50 transmits various control signals (e.g., starting wavelength in scanning, end wavelength in scanning, scanning rate, etc) to the spectroscope 12 to begin spectral measurement.

In the sample S, various phenomena occurs, such as absorption, reflection and interference of light, which depends on the wavelength of the probe light. The present invention attaches importance to a change of an optical reflection spectrum peculiar to excitons.

The computer 50 receives the detection signal supplied during spectral measurement to store it in a memory, and then, after the measurement, to convert the detection signal into a reflectance spectrum using the above-mentioned equation (1), and if needed, to indicate it on the display 51. Further, a broadening factor of the exciton spectral feature is extracted by analyzing the reflectance spectrum of the sample S using equations (2), (3) and (4).

The computer 50 stores beforehand data of a standard sample, which exhibits a known relation between a surface state (e.g., crack density) and a broadening factor of an exciton spectral feature. Hence, the surface state of the sample S can be evaluated quantitatively by comparing the resultant broadening factor of the sample S with the broadening factor of the standard samples.

Subsequently, in changing the measurement area of the sample S, the adjusting mechanism 22 operates to move the sample S so that the irradiation position of the probe light is changed. Then, spectrum measurement and analysis will be performed according to such procedures as described above. This repetition of two-dimensional scanning and spectrum measurement for the sample S enables distribution of defect in the whole surface of the sample S to be evaluated.

Embodiment 3

Figure 5:
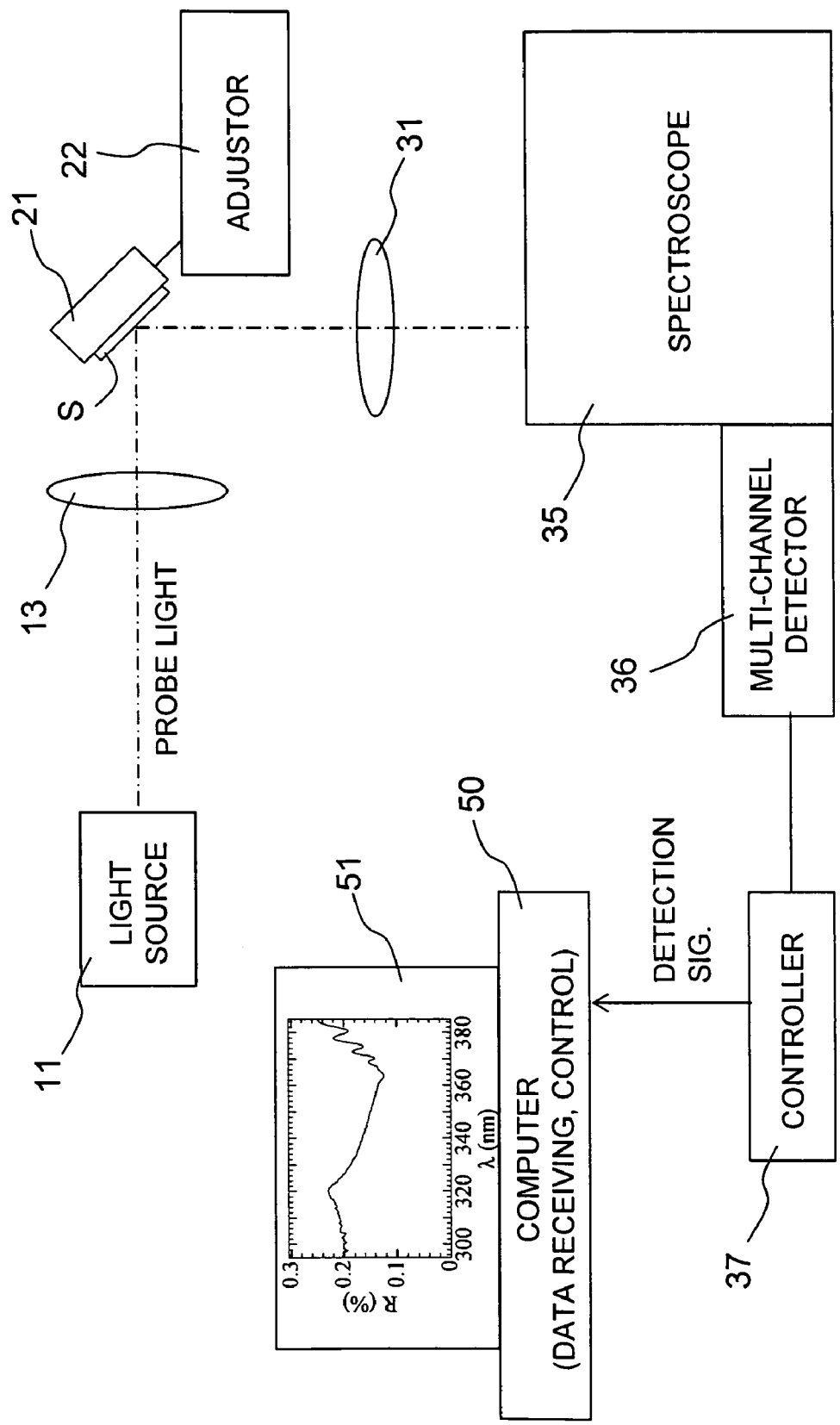
FIG. 5 is a block diagram showing another example of an surface evaluating apparatus according to the present invention.

FIG. 5 is a block diagram showing another example of an surface evaluating apparatus according to the present invention. The surface evaluating apparatus includes light source 11, sample stage 21, spectroscope 35, multi-channel detector 36, and computer 50.

The light source 11 generates probe light with the continuous spectrum that covers a wavelength range required for spectrum measurement. The probe light is focused onto the measurement area of the sample S with a desired spot size.

The sample stage 21 holds the sample S so as to adjust the three-dimensional position (X-Y-Z directions) or angles (pitch, yaw and roll) of the sample S using adjusting mechanism 22. The adjusting mechanism 22 may be manually operated or be operated according to a control signal from the computer 50.

The light reflected from the sample S is collected into the spectroscope 35 by condenser lens 31, and then inputted to the multi-channel detector 36. The spectroscope 35 is constituted of a diffraction grating or a prism, and functions so as to spatially resolve in wavelength the continuous spectrum light. The multi-channel detector 36 is constituted of a linear array of a number of detecting faces being arranged in line, and can detect distribution of intensity of light which is spatially resolved by the spectroscope 35. Therefore, in case of using the multi-channel detector 36, there is no need of wavelength scanning, which enables high speed spectrum measurement.

Controller 37 processes an output signal of the multi-channel detector 36 to transmit a detection signal to the computer 50.

The computer 50 receives the detection signal from the controller 37 to store it in a memory or the like, and if needed, indicate the data on a display 51.

This surface evaluating apparatus can operate based on the flow chart shown in FIG. 1. First, the sample S, for example, the nitride semiconductor wafer as shown in FIG. 2, is attached onto the sample stage 21. Next, the sample S is irradiated with the probe light from the light source 11, and then the multi-channel detector 36 outputs a reflection spectrum of the sample S.

The computer 50 receives the detection signal supplied from the multi-channel-detector 36 to store it in a memory, and then, after completion of measurement, to convert the detection signal into a reflectance spectrum using the above-mentioned equation (1), and if needed, to indicate it on the display 51. Further, a broadening factor of the exciton spectrum is extracted by analyzing the reflectance spectrum of the sample S using equations (2), (3) and (4).

The computer 50 stores beforehand data of a standard sample, which exhibits a known relation between a surface state (e.g., crack density) and a broadening factor of an exciton spectral feature. Hence, the surface state of the sample S can be evaluated quantitatively by comparing the resultant broadening factor of the sample S with the broadening factor of the standard samples.

Subsequently, in changing the measurement area of the sample S, the adjusting mechanism 22 operates to move the sample S so that the irradiation position of the probe light is changed. Then, spectrum measurement and analysis will be performed according to the above-described procedures. This repetition of two-dimensional scanning and spectrum measurement enables distribution of defect in the whole surface of the sample S to be evaluated.

Embodiment 4

Figure 6:
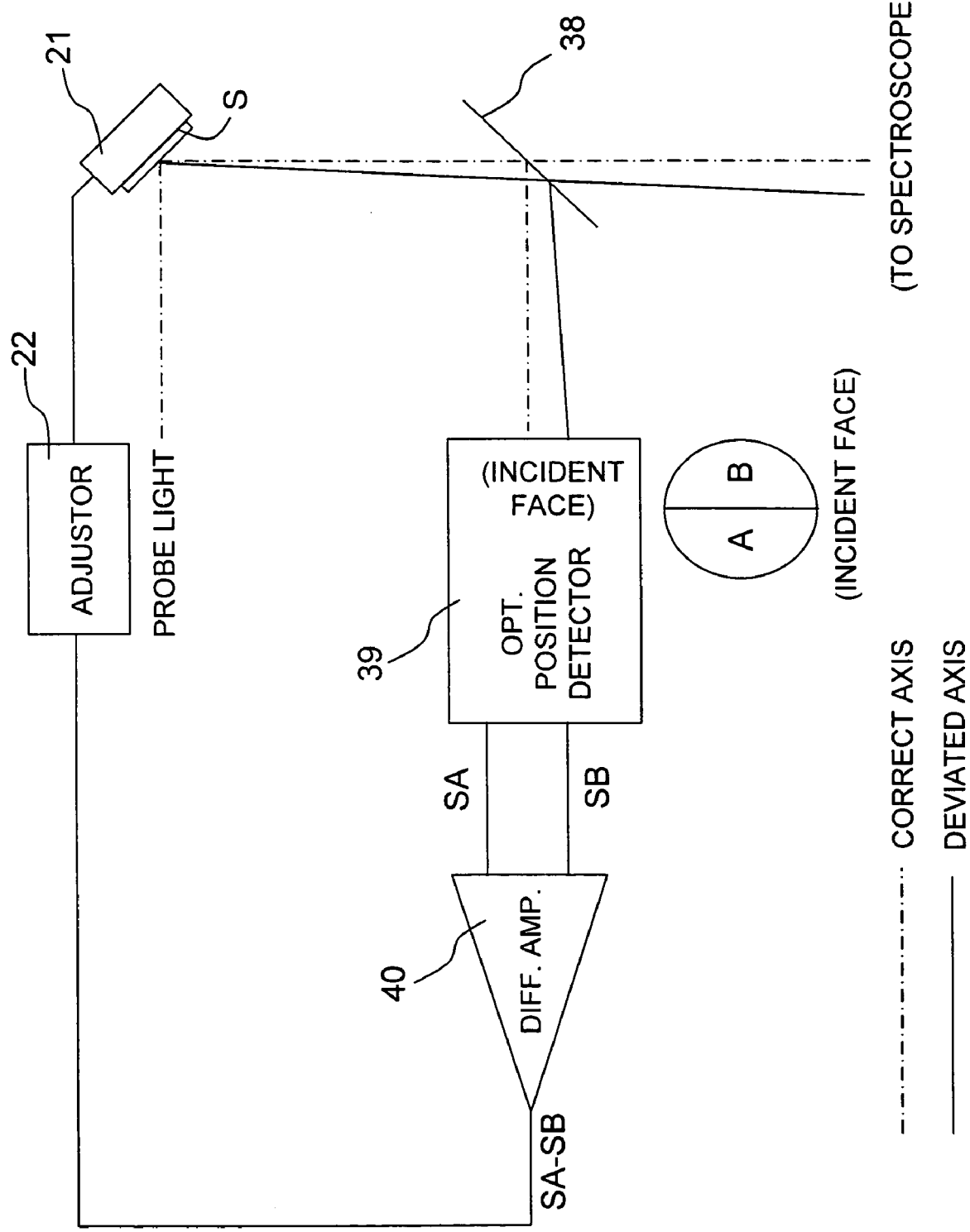
FIG. 6 is a configuration diagram showing an example of an optical path correction mechanism for reflected light.

FIG. 6 is a configuration diagram showing an example of an optical path correction mechanism for reflected light. This optical path correction mechanism can be applied to the surface evaluating apparatus shown in FIGS. 4 and 5.

An optical path detection apparatus includes splitting optical device 38, optical position detector 39, and differential amplifier 40.

The splitting optical device 38, which may be composed of a beam splitter or the like, functions to pick up a part of the reflected light from the sample S. The optical position detector 39, which may be composed of a PSD (position sensitive device) or a division type detector, detects a position of light picked up by the splitting optical device 38. Herein exemplified is a dual division type detector in which two detecting faces A and B are arranged, alternatively, it may be a quadrant division type detector in which four detecting faces are arranged along X-Y directions.

The differential amplifier 40 is constituted of an operational amplifier or the like, and differentially amplifies two signals SA and SB out of the optical position detector 39 to output a difference signal (SA-SB).

This optical path detection apparatus can precisely detect a deviation of the reflected light with little influence on the light reflected from the sample S. Further, it is preferable that the optical length from the sample S through the splitting optical device 38 to the optical position detector 39 is designed as long as possible, thereby enhancing sensitivity of the deviation of the reflected light.

The optical path correction mechanism includes the above-described optical path detection apparatus, and the adjusting mechanism 22 for adjusting the three-dimensional position (X-Y-Z directions) or angles (pitch, yaw and roll) of the sample stage 21.

Next, feedback operation of the optical path correction mechanism is described below. In using a wafer, on which semiconductor layers are formed, for the sample S, flatness of the wafer must be taken into account. In particular, when the wafer is warped, the optical axis of the reflected light may deviate during measuring two-dimensional distribution data, for example, from the original optical path of the reflected light, denoted by dashed lines in FIG. 6, to another optical path denoted by solid lines in FIG. 6.

More particularly, in the multi-channel photometry as shown in FIG. 5, if the optical axis of the reflected light may deviate, an angle incident to the spectroscope 35 is changed, hence the distribution of intensity of light is shifted on the array of detecting faces of the multi-channel detector 36, thereby resulting a shift in wavelength of an optical spectrum.

To cope with this problem, during two-dimensional scanning of the sample S, the above-described optical path detection apparatus detects the deviation of the optical path of the light reflected from of the sample S and the adjusting mechanism 22 adjusts the position or the angle of the sample stage 21 so as to eliminate the deviation of the optical path, thereby reducing or eliminating a measurement error due to the warp of the wafer.

Figure 7:
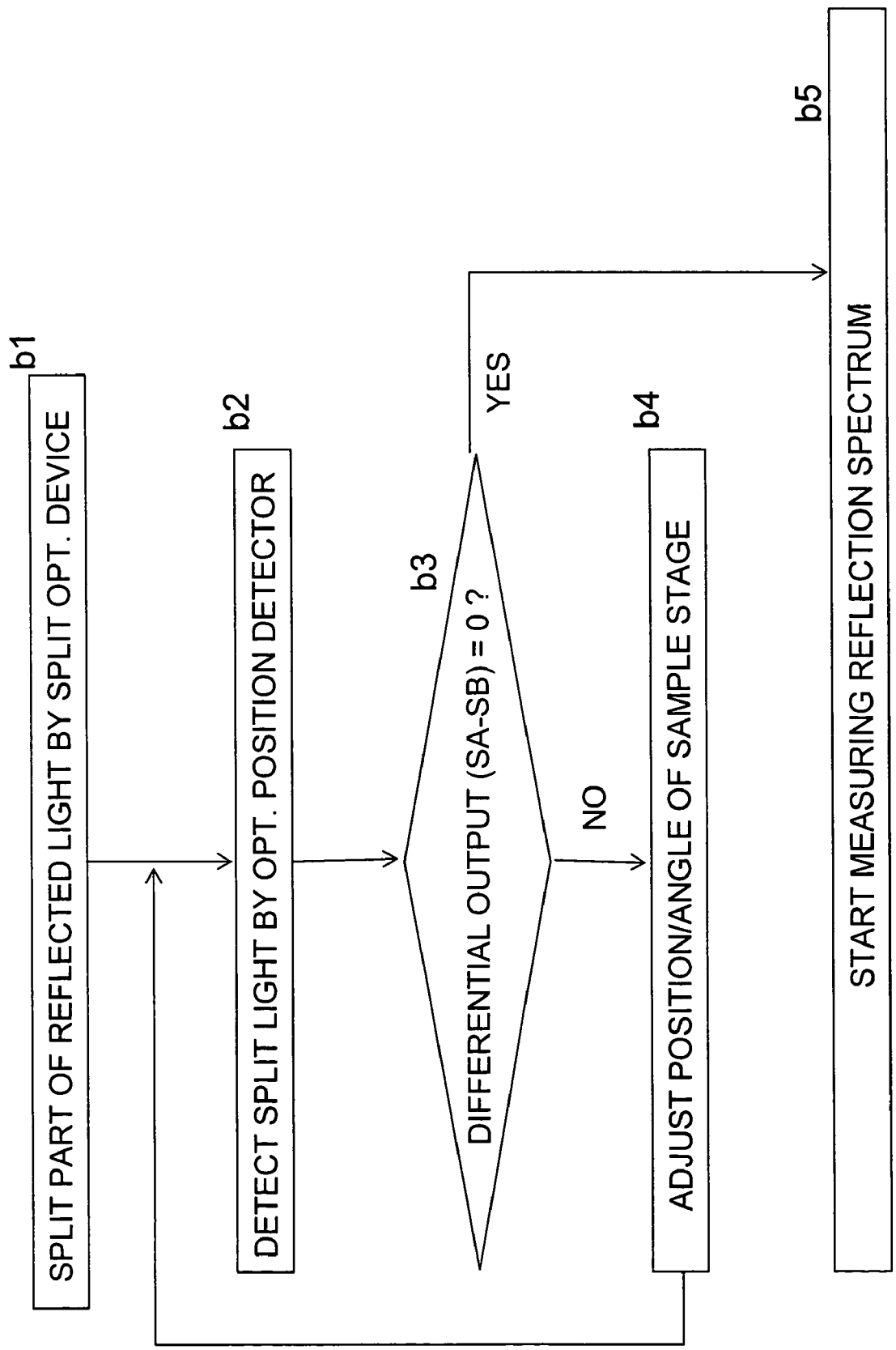
FIG. 7 is a flow chart showing operation of the optical path correction mechanism.

FIG. 7 is a flow chart showing operation of the optical path correction mechanism. First, in step b1, part of the reflected light from the sample S is divided by the splitting optical device 38. Next, in step b2, the optical position detector 39 receives the divided light to detect the position of the light. Next, step b3 judges whether the difference signal (SA-SB) of the differential amplifier 40 is zero or not. In a case of the difference signal being not zero, moving to step b4, the adjusting mechanism 22 adjusts the position or the angle of the sample stage 21 so that the difference signal approaches zero, and then returning to the step b2 to repeat detection of the optical position and adjustment of the sample stage. After the difference signal converges at zero by this feedback operation, moving from the step b3 to step b5 to start spectrum measurement of the sample S.

Subsequently, in changing the measurement area of the sample S, the adjusting mechanism 22 operates to move the sample S in the plane so that the irradiation position of the probe light is changed. Then, a deviation of the reflected light is eliminated by operation of the optical path correction shown in FIG. 7, and then spectrum measurement and analysis will be performed according to the above-described procedures. This sequential repetition of two-dimensional scanning, optical path correction and spectrum measurement for the sample S enables distribution of defect in the whole surface of the sample S to be evaluated.

Examples

Figure 8A:
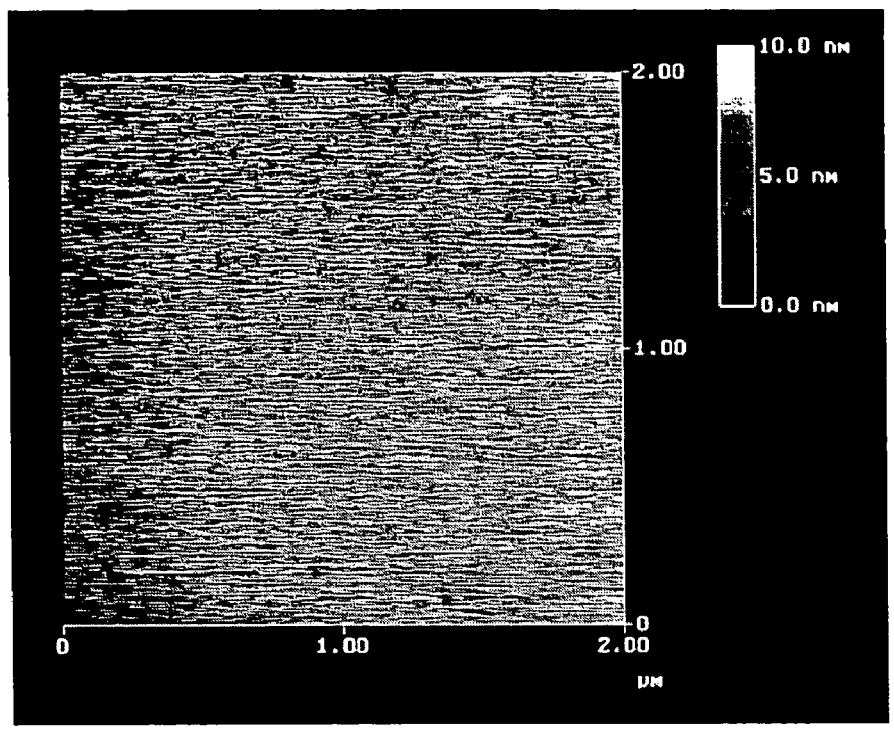
FIGS. 8A and 8B are photographs showing images of HEMT epitaxial structures of AlGaN/GaN which are observed by AFM, respectively.
Figure 8B:
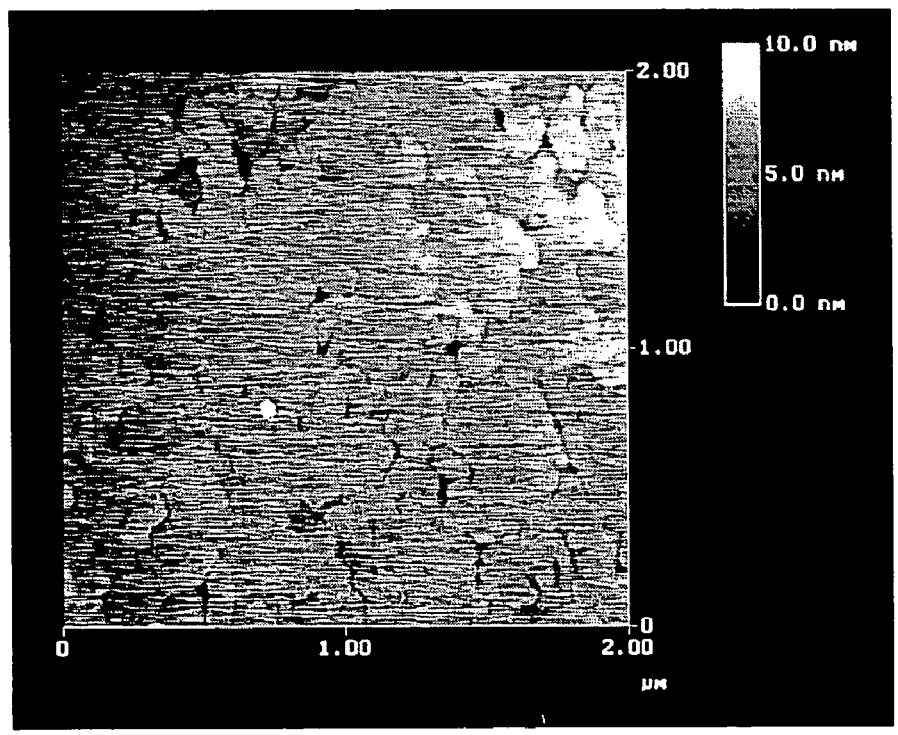

FIGS. 8A and 8B are photographs showing images of HEMT epitaxial structures of AlGaN/GaN which are observed by AFM. The grayscale of the image corresponds to height of the surface. Incidentally, it took 30 minutes to complete acquiring each of these AFM images.

The sample A, whose AFM image is shown in FIG. 8A, exhibits a flat surface and no crack, therefore, it can be used for a standard sample. The sample B, as shown in FIG. 8B, exhibits concavity and convexity on the surface and a number of cracks.

Figure 9:
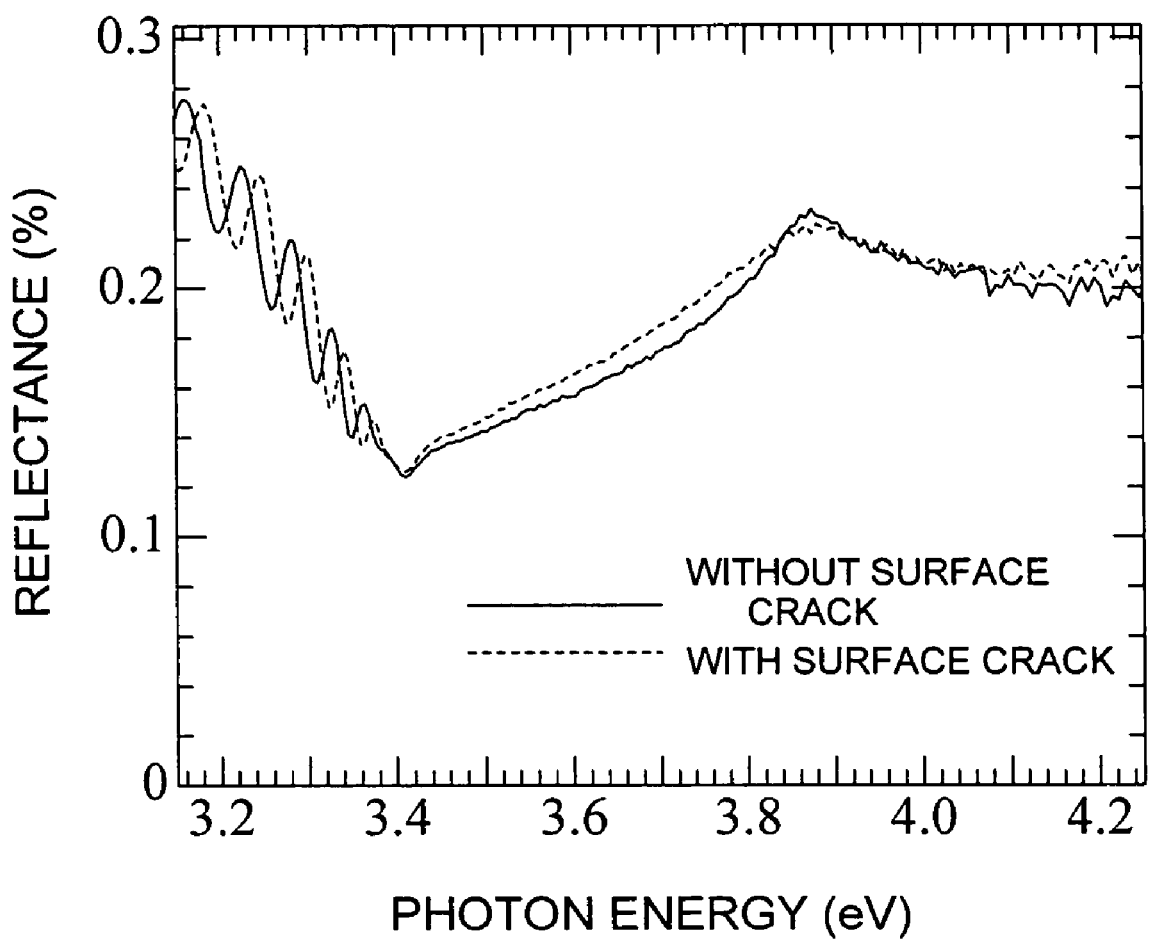
FIG. 9 is a graph showing optical reflection spectra of samples A and B.

FIG. 9 shows the optical reflection spectra of the samples A and B. The vertical axis denotes reflectance (%) and the horizontal axis denotes photon energy (eV). The solid curve shows the reflected spectra of sample A having no crack on the surface. The dashed curve shows the reflected spectra of sample B having cracks on the surface. These spectra was measured using the surface evaluating apparatus shown in FIG. 4. It took 3 minutes, i.e., 1/10 of the AFM observation, to measure each of the spectra.

The exciton-related features are located about 3.87 eV (≈320 nm). The spectrum (dashed curve) of the sample B having cracks looks broader as compared to the spectrum (solid curve) of the sample A having no crack.

Figure 10A:
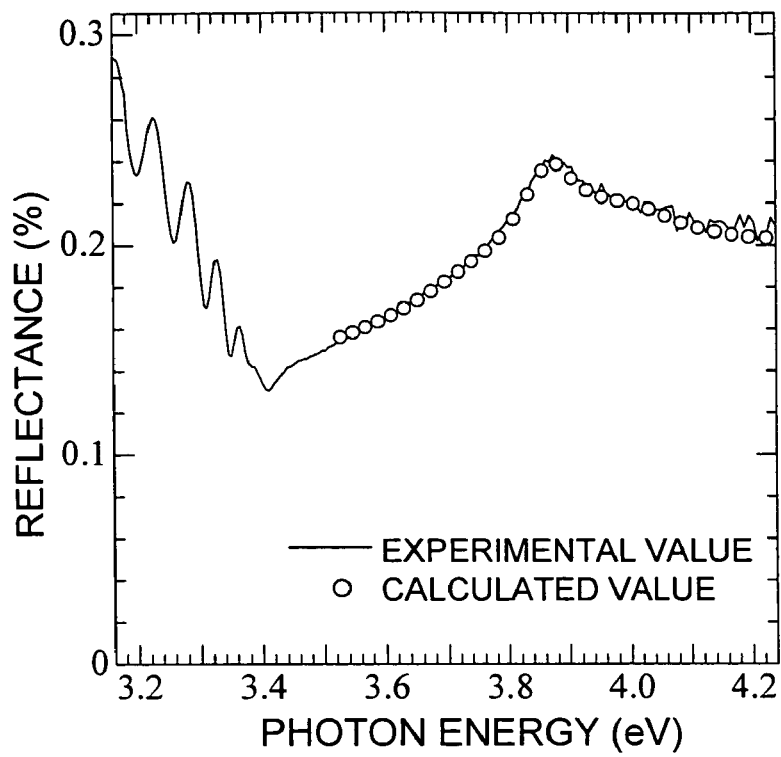
FIGS. 10A and 10B are graphs showing results of fitting the optical reflection spectra of the samples A and B in FIG. 9, respectively.
Figure 10B:
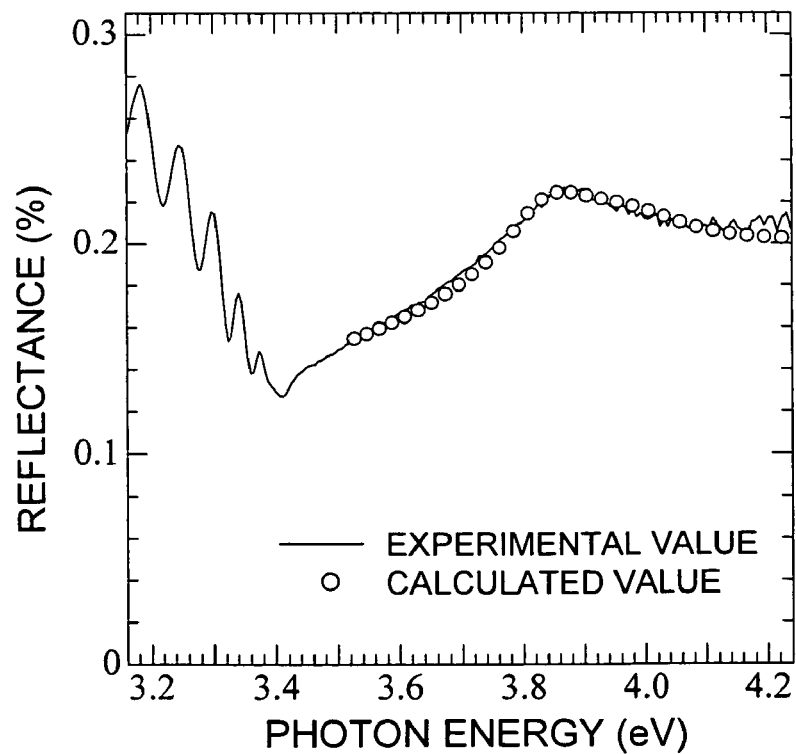

FIGS. 10A and 10B show results of fitting the optical reflection spectra of the samples A and B in FIG. 9, respectively. The solid curve shows experimental values of respective reflection spectra in FIG. 9. The white circles show values calculated by a computer using the above-mentioned equations (3) to (4).

Both of the fitting curve of the sample A shown in FIG. 10A and the fitting curve of the sample B shown in FIG. 10B coincide significantly with the experimental values thereof around the exciton-related features. As a result, the broadening factors are estimated to be 25 meV for sample A and 45 meV for sample B. Accordingly, it is apparent that the larger density of crack on the surface exhibits the larger broadening factor.

As described above, when evaluating a surface state of a sample, calculation of a broadening factor of the exciton spectrum can attain quantitative evaluation more quickly with higher accuracy in comparison to the conventional AFM observation method.

Embodiment 5

In the above description, a quantitative evaluation method of semiconductor surfaces using reflectance spectroscopy was explained. This is a method for quantifying a surface state based on a broadening factor of reflection spectrum, that is, a method for quantifying a surface state using a characteristic index of sharpness of a spectral shape. Sharpness of the spectral shape corresponds to intensity of the differential signal thereof. Therefore, measurement of a differential signal of the reflection spectrum, i.e., a modulated reflection spectrum enables the surface state to be quantified using a characteristic index of spectral intensity. In general, a differential signal is more sensitive to variation. Hence, information on the surface state, which cannot be obtained by an ordinary reflection spectrum, can be extracted. Hereinafter, a quantitative evaluation method of semiconductor surfaces using modulation reflectance spectroscopy is be explained.

Modulation optical reflectance measurement includes various approaches. Specifically, PR (photo reflectance) spectroscopy (optical modulation reflectance spectroscopy) is a nondestructive, non-contact and the most convenient approach. PR measurement is characterized in that a sample surface is irradiated with excitation light as well as probe light for detecting a reflectance. Carriers generated by the excitation light can slightly change an internal electric field of the sample due to the shielding effect thereof. In general, changing of the internal electric field may vary optical constants of the sample. PR measurement can measure a slight change of an optical constant as a modulated reflectance. The resultant PR signal can be roughly classified into two signals of FK (Franz-Keldysh) oscillations and a third derivative shape signal on condition that there is only the internal electric field which does not affect the band structure.

The FK oscillations and the third derivative shape signal can be observed in each case of the following equations (7) and (8) using two characteristic indices of an electro-optic coefficient shown by the following equation (5) and a lifetime broadening factor Γ, where e is an elementary electric charge, h is a Planck's constant, F is an intensity of internal electric field, and μ is a reduced mass of electron and hole.

$$\hbar\Omega = \left(\frac{e^2\hbar^2 F^2}{8\mu}\right)^{1/3} \quad (5)$$

$$\hbar = \frac{h}{2\pi} \quad (6)$$

$$\hbar\Omega \gg \Gamma \quad (7)$$

$$\hbar\Omega \ll \Gamma \quad (8)$$

Figure 11:
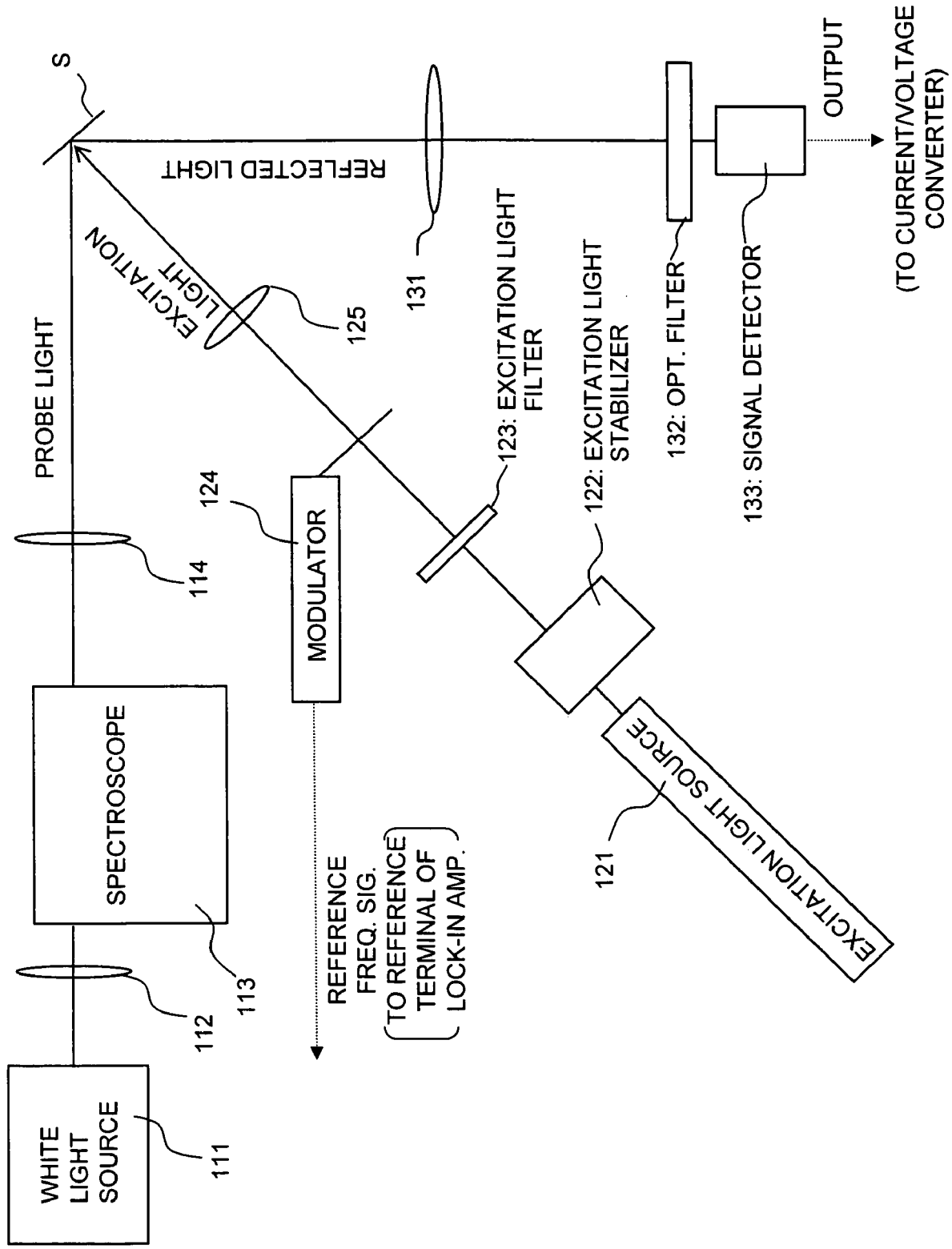
FIGS. 11 and 12 show schematic views of a spectroscope apparatus.
Figure 12:
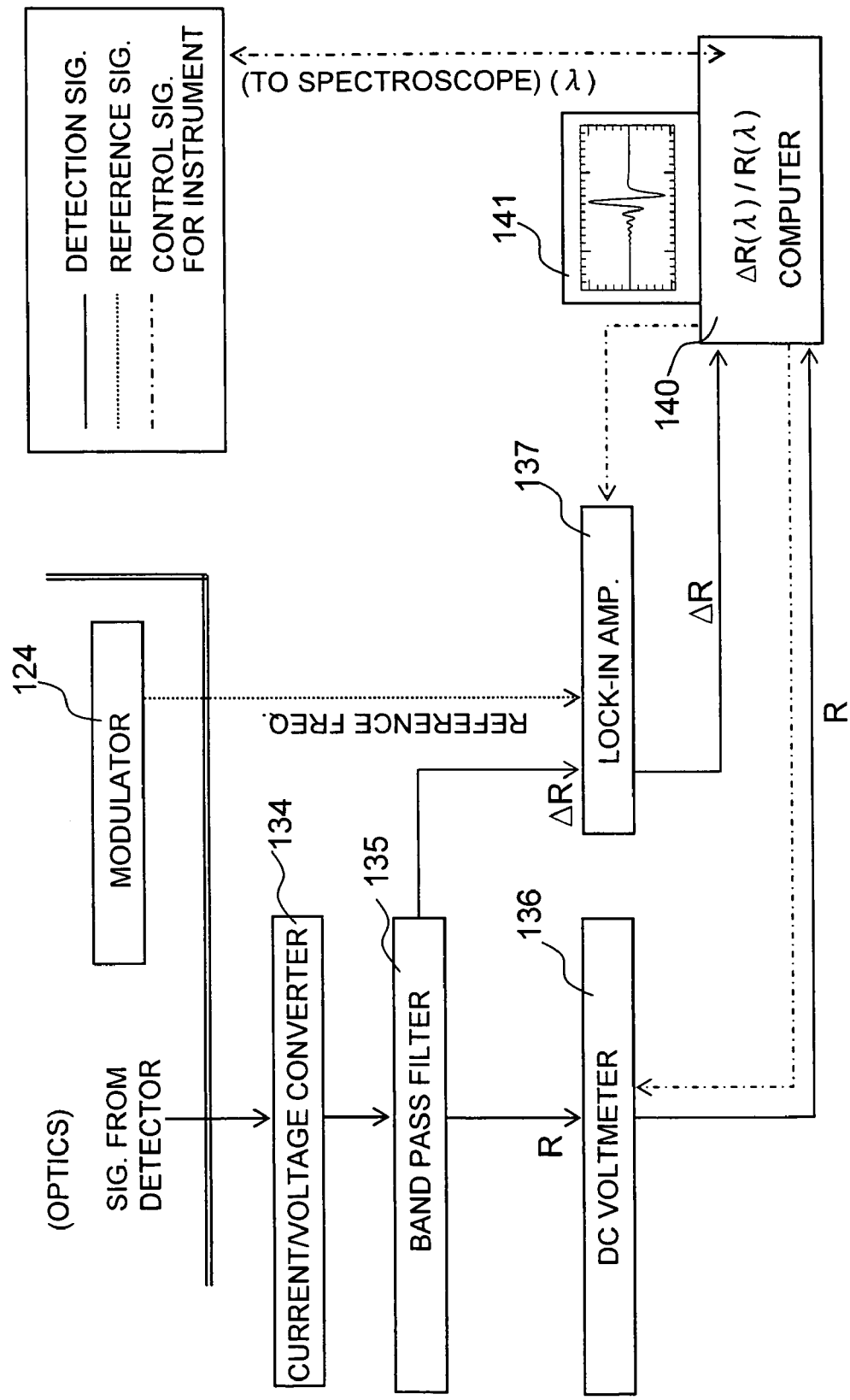

FIGS. 11 and 12 show schematic views of a spectroscope apparatus for measuring the PR signal. The PR spectroscope system is provided with an excitation light source, a modulator and a lock-in amplifier for measuring a modulated reflection signal, additional to the apparatus for measuring reflection spectrum, as shown in FIG. 4.

An optics system of probe light includes white light source 111, condenser lens 112, spectroscope 113, and condenser lens 114. The white light source 111, e.g., a lamp, generates light with the continuous spectrum that covers a wavelength range required for spectral measurement. The spectroscope 113 disperses the light provide from the white light source 111 to supply monochromatic probe light. The wavelength of the probe light can be changed continuously according to a control signal from computer 140. The probe light from the spectroscope 112 is focused onto the measurement area of sample S with a desired spot size.

An optics system of excitation light includes excitation light source 121, excitation light stabilizer 122, excitation light filter 123, modulator 124, and condenser lens 125. The excitation light source 121, e.g., a laser light source, provides excitation light of a wavelength shorter than a wavelength corresponding to band-gap energy of the sample S in order to generate carriers through the photo absorption in the sample S. The excitation light stabilizer 122 functions to stabilize the power of the excitation light from the excitation light source 121. The excitation light filter 123 is a band pass filter which passes the wavelength of the excitation light through and cuts noise light off. The modulator 124 modulates the intensity of the excitation light based on a predetermined reference frequency signal. The light passing through the modulator 124 is focused with a desired spot size onto the sample S by the condenser lens 125 so as to be superimposed on the measurement area of the probe light.

An optics system for detection includes condenser lens 131, optical filter 132, and signal detector 133. The light reflected from the sample S is focused onto the signal detector 133 by the condenser lens 131. The intervening optical filter 132 is a long pass filter which cuts the excitation light off and passes only the probe light through, which can be detached, if needed.

A signal processing system, as shown in FIG. 12, includes current-voltage converter 134, band pass filter circuit 135, DC voltmeter 136, lock-in amplifier 137, computer 140, and display 141. The signal detector 133 functions as to convert intensity of light into an electric signal, and then the current signal from the signal detector 133 is converted into a voltage signal by the subsequent current-voltage converter 134. The band pass filter circuit 135 can separate both of a DC component, corresponding to reflectance R, and an AC component, corresponding to modulation reflectance ΔR, from the detection signal. The DC voltmeter 136 measures a voltage of the DC component of the detection signal, and converts it into a digital signal for the computer 140. The lock-in amplifier 137 can measure a component with frequency equal to the reference supplied from the modulator 124, in the AC component of the detection signal, and digitizes it for the computer 140. The computer 140 receives both of the reflectance signal R from the DC voltmeter 136 and the modulation reflectance signal ΔR from the lock-in amplifier 137, and stores them in a memory or the like, and if needed, indicates the data on the display 141.

Figure 13:
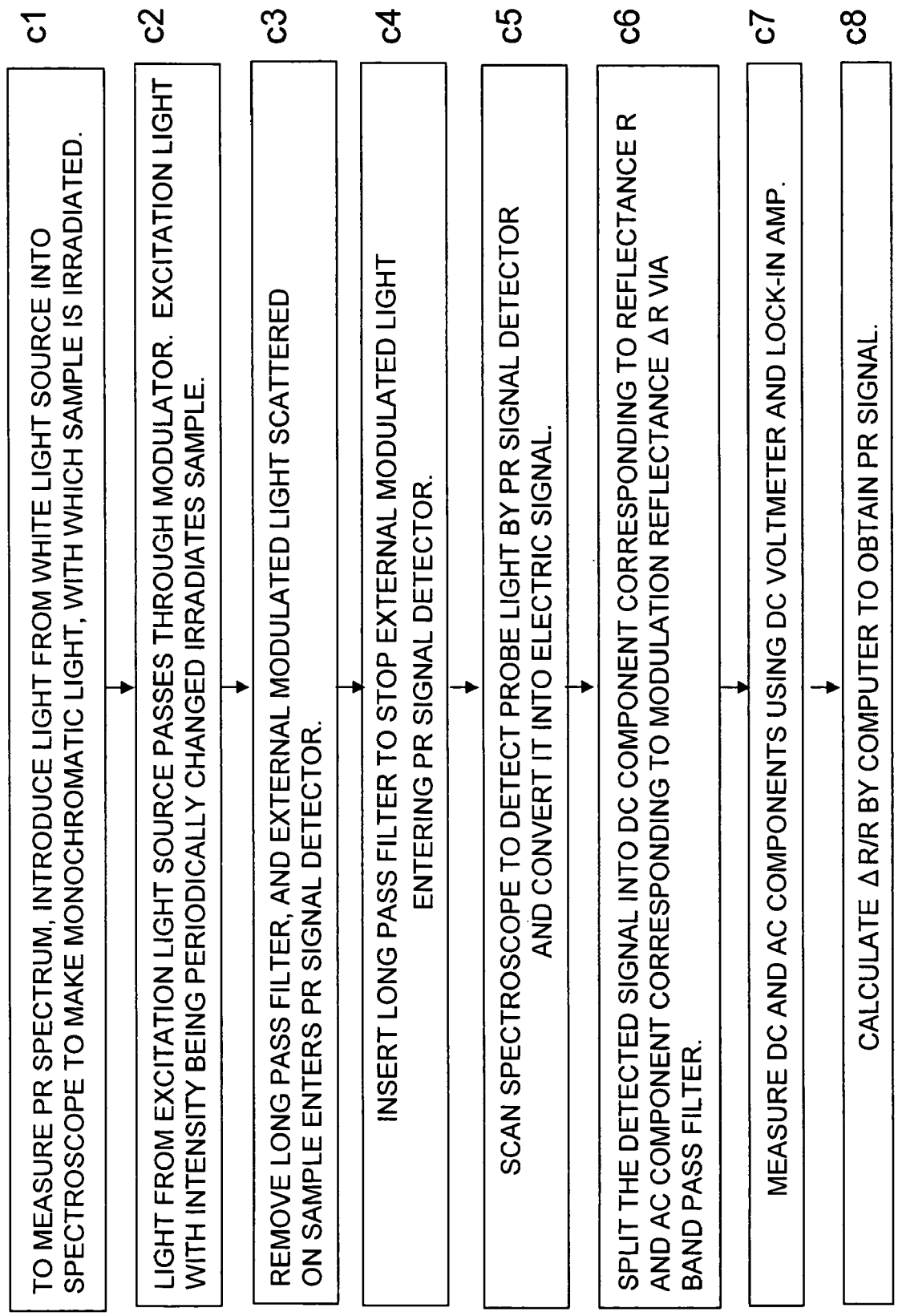
FIG. 13 is a flow chart showing an example of procedure of PR spectroscopy measurement.

The PR spectrum is measured according to a flow chart shown in FIG. 13. Procedure of the PR spectroscopic measurement is described below in detail according to the flow chart shown in FIG. 13.

The probe light for detecting the reflectance of the sample S is obtained by introducing light from the white light source 111 into the spectroscope 113 to make monochromatic light. The monochromatic probe light irradiates the sample S via the condenser lens 114 (step c1). Meanwhile, the excitation light is converted by the modulator 124 so that the intensity thereof varies periodically in time, and then irradiates the sample S (step c2).

The lock-in amplifier 137 for detecting the PR signal requires phase adjustment. In order to perform the phase adjustment, the optical filter 132 in front of the detector is removed from the optical axis, so that excitation light scattered on the sample S can enter the signal detector 133. The phase adjustment of the lock-in amplifier 137 is performed so as to synchronize the signal detected in this state with the reference frequency signal supplied from the modulator 124 (step c3). After the phase adjustment, the optical filter 132 is inserted into the optical axis to cut the scattered excitation light off, so that only the probe light can enter the signal detector 133 (step c4).

The above setting is followed by measurement of data. First, the spectroscope 113 starts scanning while the probe light reflected on the sample S is converted into the electric signal by the signal detector 133 (step c5). The resultant signal is split into the DC component corresponding to the reflectance R and the AC component corresponding to the modulation reflectance ΔR through the band pass filter circuit 135 (step c6), which are measured by the DC voltmeter 136 or the lock-in amplifier 137, respectively (step c7). The computer 140 calculates ΔR/R using each measured value and plots it as a function of photon energy or wavelength to obtain the PR spectrum (step c8).

Figure 14:
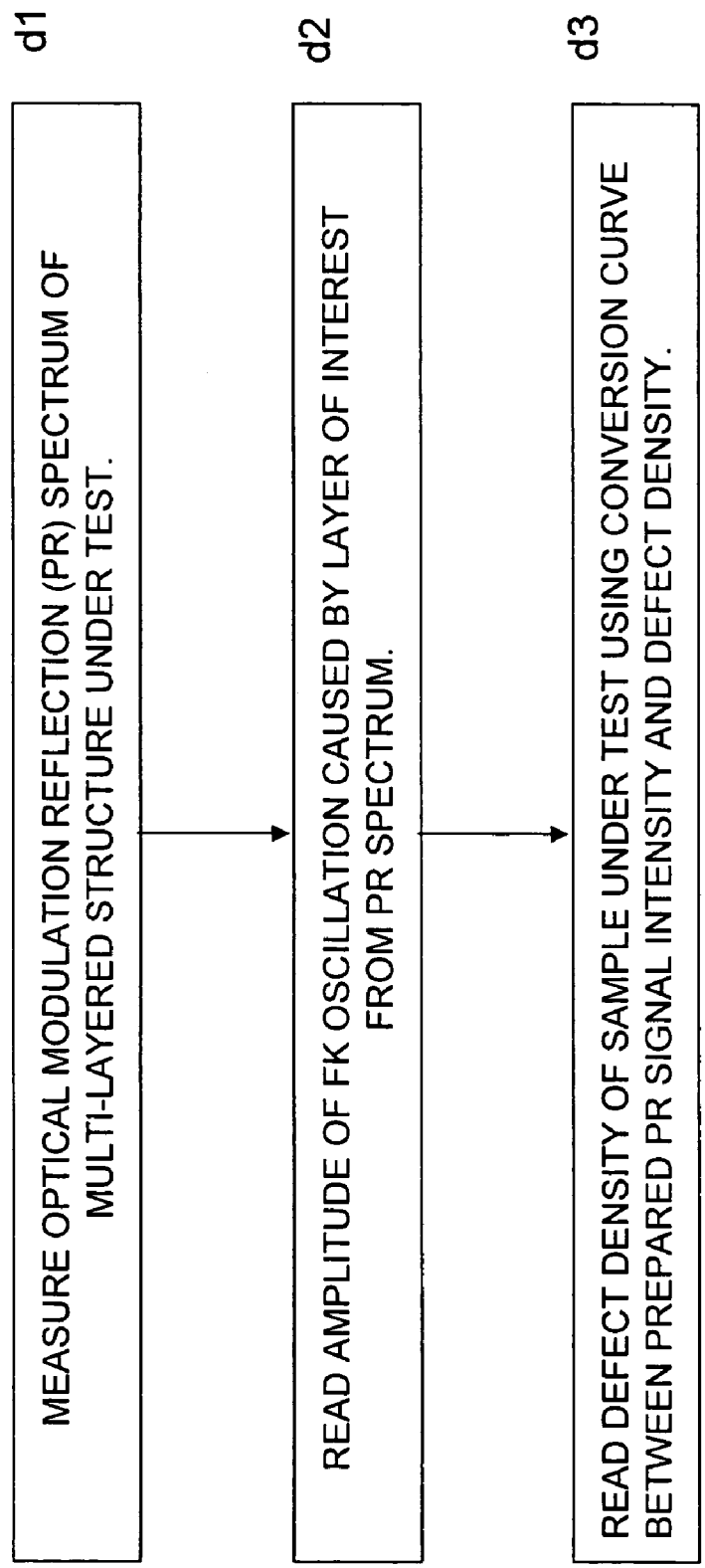
FIG. 14 is a flow chart showing an example of procedure for obtaining density of defect from PR spectrum.

FIG. 14 shows a flow chart for obtaining density of defect from the resultant PR spectrum. First, the PR spectrum is measured as described above (step d1), followed by reading from the resultant spectrum amplitude of the third derivative lineshape signal or the FK oscillation profile caused by a layer of interest (step d2). The FK oscillation profile typically consists of a plurality of oscillations. For analysis, choice of an oscillation with the best signal to noise ratio, that is, the largest amplitude in the profile may ensure precision of values resulting from the analysis. The oscillation with the largest amplitude appears around the band gap energy of the layer of interest, therefore, it is suitable to estimate the amplitude from this oscillation. Hereinafter the amplitude of the FK oscillation or the third derivative lineshape shape signal will be simply referred to as PR signal intensity, unless otherwise denoted.

Figure 15:
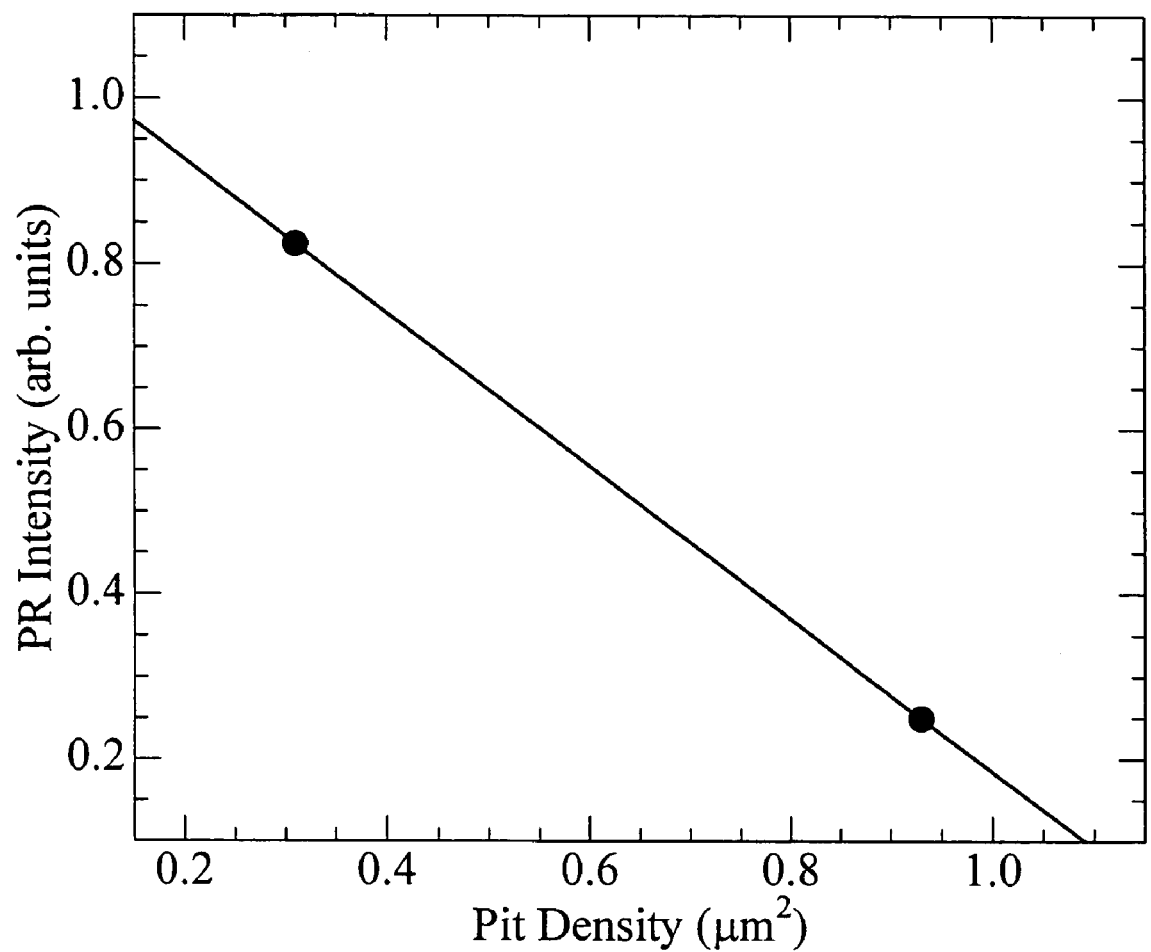
FIG. 15 is a conversion curve showing a relation between density of defect and PR signal intensity.

Finally, the density of defect is obtained from the resultant PR signal intensity (step d3). In the resultant spectrum, as described above, the amplitude of the FK oscillation profile resulting from the layer of interest depends on a state (crystallinity, etc) of the layer of interest. Then, PR measurement of a standard sample having a known density of defect is performed in advance to prepare a conversion curve (FIG. 15) with the horizontal axis corresponding to density of defect and the vertical axis corresponding to PR signal intensity. The density of defect can be obtained by comparing the PR signal intensity of the sample under test with an working curve, based on the conversion curve.

Embodiment 6

Figure 16:
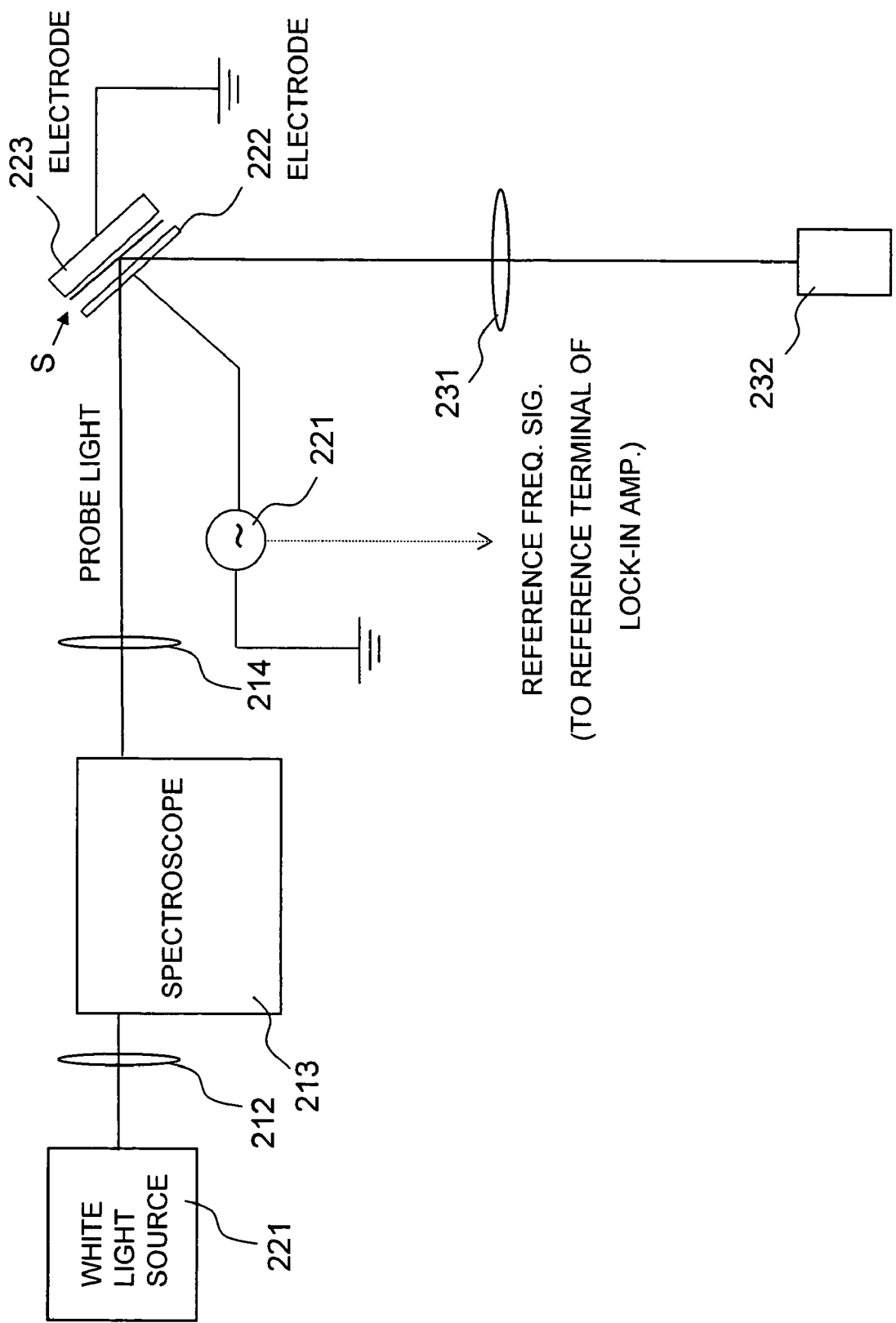
FIG. 16 is a schematic view showing an example of a CER spectroscope apparatus.

The above-described PR measurement is most widely utilized among various optical modulation reflectance spectroscopic techniques. However, the PR measurements are sometimes inapplicable: for example, the case where no light source for exciting a sample is available. Furthermore, in another case of a sample exhibiting strong emission caused by irradiation of excitation light. The emission behaves like a disturbance component, which makes it difficult to obtain a PR spectrum. In this case, CER (Contactless electroreflectance) spectroscopy is applicable among various optical modulation reflectance spectroscopic techniques. FIG. 16 shows a schematic view of the CER spectroscope apparatus. Incidentally, the system shown in FIG. 12 can be used for the signal processing system thereof, illustration of which is omitted.

An optics system of probe light includes white light source 211, condenser lens 212, spectroscope 213, and condenser lens 214. The white light source 211, e.g., a lamp, generates light with the continuous spectrum that covers a wavelength range required for spectral measurement. The spectroscope 213 disperses the light provide from the white light source 211 to supply monochromatic probe light. The wavelength of the probe light can be changed continuously according to a control signal from the computer 140 shown in FIG. 12. The probe light from the spectroscope 212 is focused onto the measurement area of sample S with a desired spot size.

An electric field applying circuit includes an AC power supply 221, and a pair of electrodes 222 and 223, which are placed to sandwich the sample S. The electrode 222, which is located on an incident light side of the sample S, is generally refereed to as transparent electrode, and formed of conductive material transparent to the probe light, and electrically connected to one terminal of the AC power supply 221. The other terminal of the AC power supply 221 is grounded. The electrode 223, which is located on the back side of the sample S, is also grounded via a sample stage.

An optics system for detection includes condenser lens 231, and signal detector 232. The light reflected from the sample S is focused on the signal detector 232 by the condenser lens 231. The detection signal from the signal detector 232 is transmitted to the signal processing system shown in FIG. 12.

Figure 17:
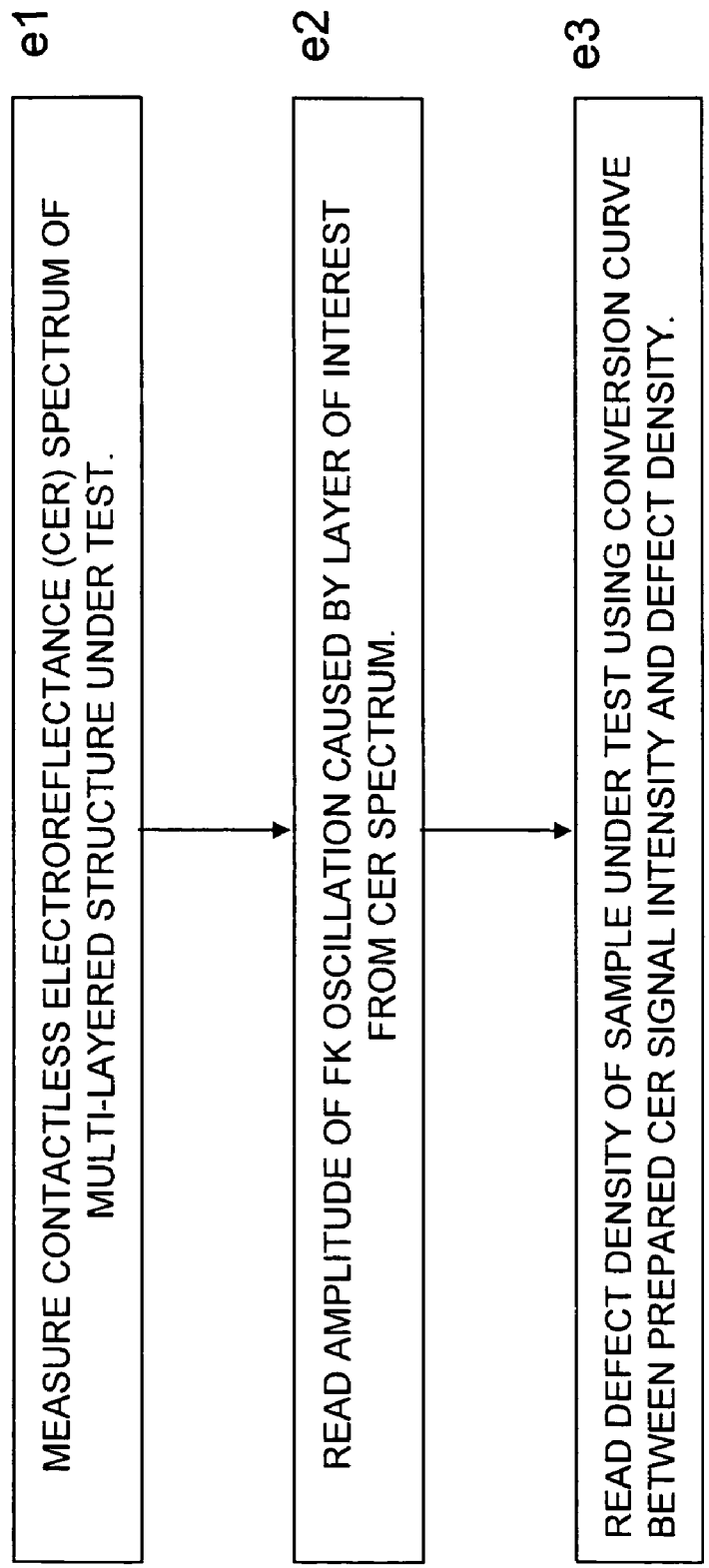
FIG. 17 is a flow chart showing an example of procedure for obtaining density of defect from CER spectrum.

During the CER measurement, an alternating electric field is applied between the pair of electrodes 222 and 223 sandwiching the sample S, and then electric filed modulation is caused inside the sample S. The effect of optical reflectance modulation due to the electric filed modulation appears in the probe light. The resultant modulated reflectance is equivalent to the PR signal, therefore, a flow chart for the analysis of the CER spectrum and calculation of defect density, which is similar to the flow chart in FIG. 14, is shown in FIG. 17.

As to the procedure of the CER measurement, the probe light for detecting the reflectance of the sample S is obtained by introducing light from the white light source 211 into the spectroscope 213 to make monochromatic light. The monochromatic probe light irradiates the sample S via the condenser lens 214. Meanwhile, an alternating electric field is applied to the sample S via the pair of electrodes 222 and 223 to modulate the light reflected from the sample S. In this state, the lock-in amplifier 137 is adjusted to be in phase so that the detection signal from the signal detector 232 is synchronized with a reference frequency signal supplied from the AC power supply 221.

The above setting is followed by acquisition of data. First, the spectroscope 213 starts scanning while the probe light reflected on the sample S is converted into the electric signal by the signal detector 232. The resultant signal is split into the DC component corresponding to the reflectance R and the AC component corresponding to the modulation reflectance $\Delta R$ through the band pass filter circuit 135. The AC component is measured by the DC voltmeter 136, while the DC component is measured by the lock-in amplifier 137. The computer 140 calculates $\Delta R/R$ using each measured value and plots it as a function of photon energy or wavelength to obtain the CER spectrum.

Next, the acquisition of the CER spectrum (step e1) is followed by estimating the resultant spectrum amplitude of the third derivative lineshape signal or the FK oscillation profile originating from a layer of interest (step e2). The FK oscillation profile typically consists of a plurality of oscillations. For analysis, choice of an oscillation with the best signal to noise ratio is essential; namely, the largest amplitude may ensure precision of the analysis. The oscillation with the largest amplitude appears around the band gap energy of the layer of interest, therefore, it is suitable to estimate the amplitude from this oscillation. Hereinafter the amplitude of the FK oscillation profile or the third derivative lineshape signal will be simply referred to as CER signal intensity, unless otherwise denoted.

Finally, the density of defect is obtained from the resultant CER signal intensity (step e3). In the resultant spectrum, as described above, the amplitude of the FK oscillation profile resulting from the layer of interest depends on a state (crystallinity, etc) of the layer of interest. Then, CER measurement of a standard sample having a known density of defect is performed in advance to prepare a conversion curve with the horizontal axis corresponding to density of defect and the vertical axis corresponding to CER signal intensity. The density of defect can be obtained by comparing the CER signal intensity of the sample under test with an working curve, based on the conversion curve.

Embodiment 7

The above-described CER measurement requires an electrode transparent to the probe light. However, there may be no transparent electrode in an ultraviolet range. ITO ($In_2O_3$:Sn), an $In_2O_3$-based transparent conductive film, which is most popular as a practical transparent conductive film for electronic devices, has a band gap energy of 3.75 eV at room temperature and exhibits transparency only in a visible range. Likewise, ZnO and $SnO_2$-based transparent conductive films have a band gap energy of 3.44 eV and 3.70 eV, respectively. Accordingly, the CER measurement cannot be applied to a multi-layered structure which is composed of a material having a band gap energy larger than that of the above transparent electrode.

Even though there is a sample to which CER and PR measurements cannot be applied, modulation reflectance spectra thereof can be measured by applying a PZR (piezoreflectance) spectroscopic technique, which is based on stress/electroreflectance spectroscopy, to the sample with piezoelectricity.

Figure 18:
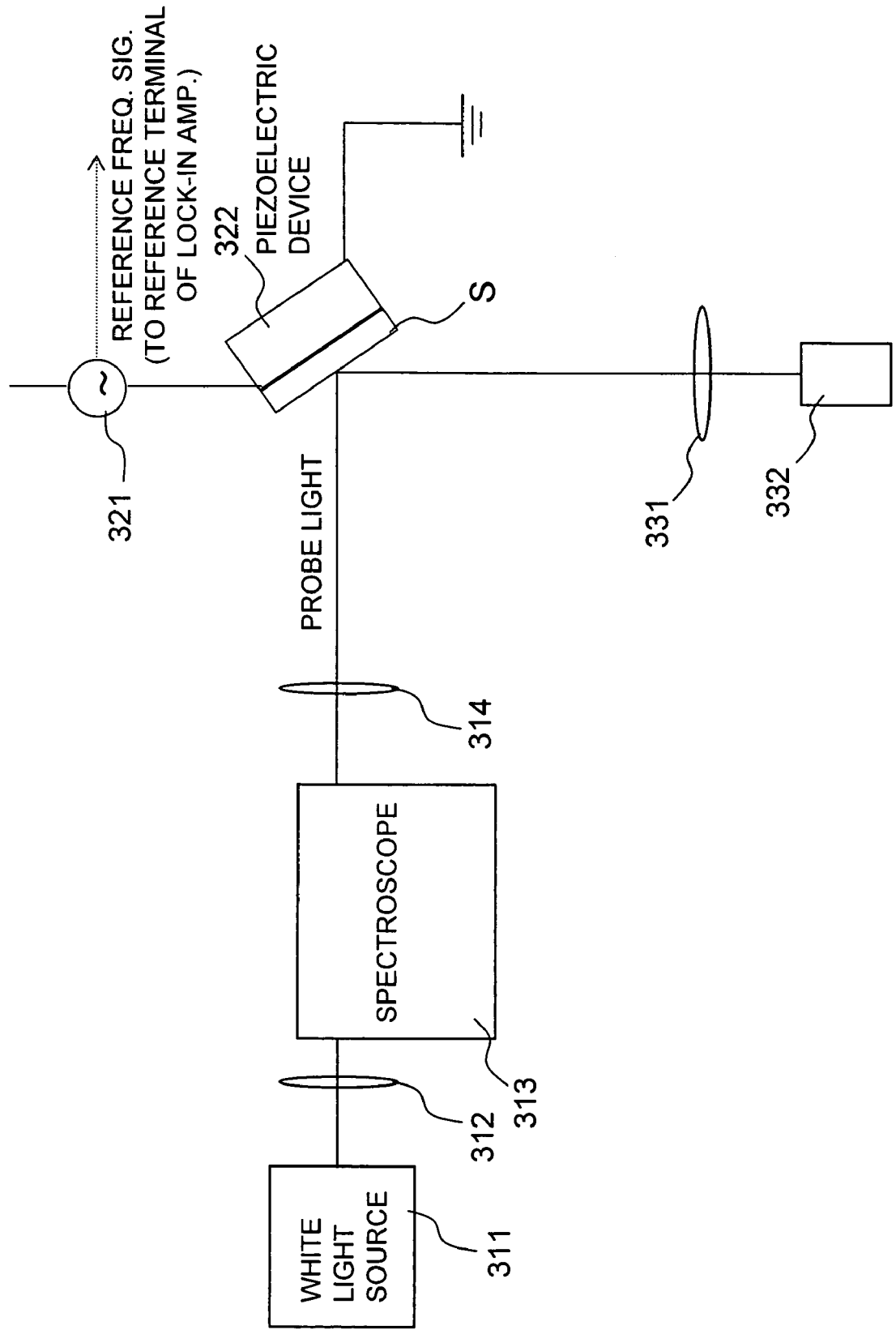
FIG. 18 is a schematic view showing an example of a PZR spectroscope apparatus.

FIG. 18 shows a schematic view of the PZR spectroscope apparatus. Incidentally, the system shown in FIG. 12 can be used for the signal processing system thereof, illustration of which is omitted.

An optics system of probe light includes white light source 311, condenser lens 312, spectroscope 313, and condenser lens 314. The white light source 311, which is composed of, e.g., a lamp, generates light with the continuous spectrum that covers a wavelength range required for spectral measurement. The spectroscope 313 disperses the light provide from the white light source 311 to supply monochromatic probe light. The wavelength of the probe light can be changed continuously according to a control signal from the computer 140 shown in FIG. 12. The probe light from the spectroscope 312 is focused onto the measurement area of sample S with a desired spot size.

A stress applying circuit includes an AC power supply 321 for generating an alternating voltage with a predetermined reference frequency, and a piezoelectric device 322 which is driven by the alternating voltage.

An optics system for detection includes a condenser lens 331, and a signal detector 332. The light reflected from the sample S is focused on the signal detector 332 by the condenser lens 331. The detection signal from the signal detector 332 is transmitted to the signal processing system shown in FIG. 12.

Figure 19:
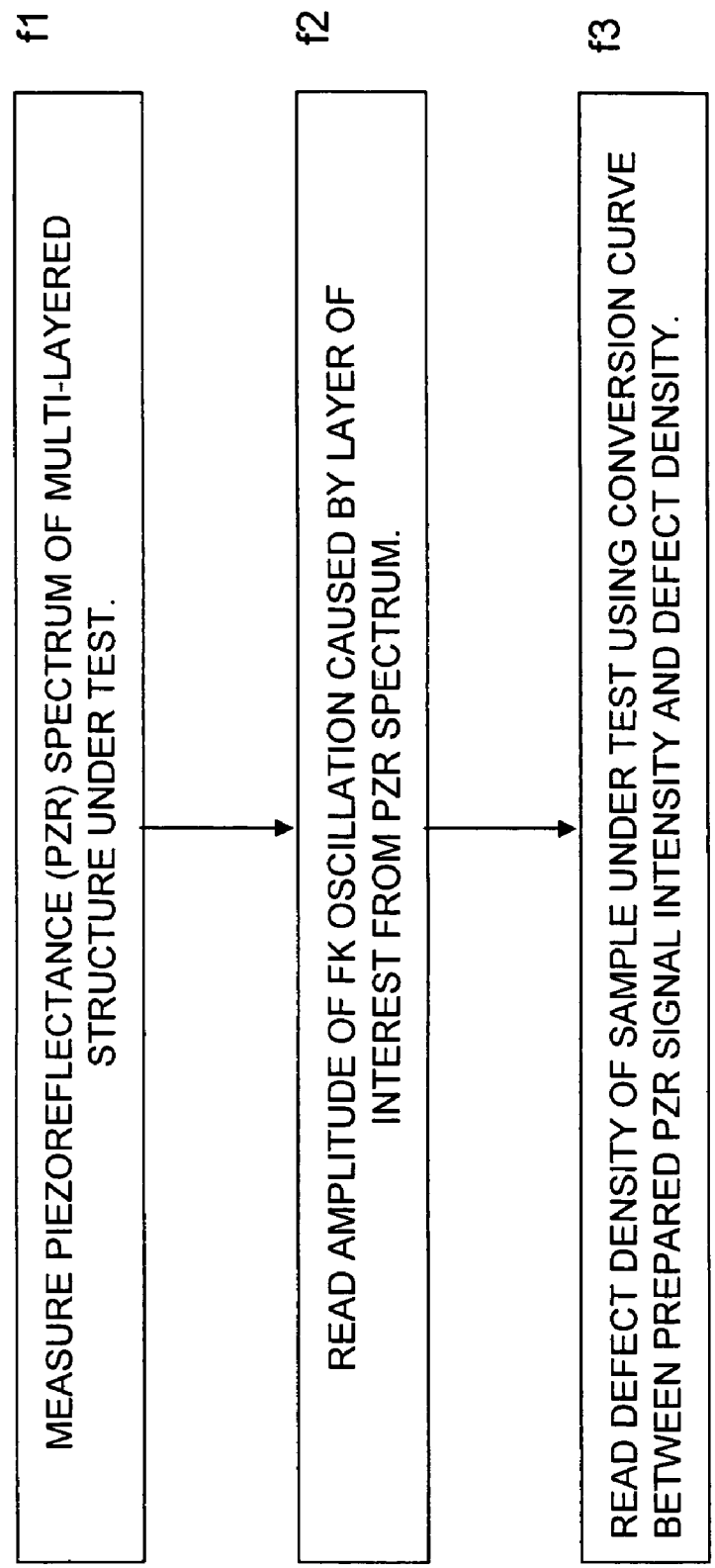
FIG. 19 is a flow chart showing an example of procedure for obtaining density of defect from PZR spectrum.

In the PZR measurement, the piezoelectric device 322, which is attached on the back side of the sample S, can generate a stress to induce periodic internal distortion in the sample S. In piezoelectric samples, periodic stresses cause a piezoelectric field leading to internal electric field modulation. Optical reflectance modulation due to the electric filed modulation can be detected by the probe light, similarly to the above-described modulation reflectance technique. The resultant modulated reflectance is equivalent to the PR signal, like the CER spectroscopy, therefore, a flow chart for analysis of the PZR spectrum and calculation of defect density, which is similar to the flow chart in FIG. 14, is shown in FIG. 19.

As to procedure of the PZR measurement, the probe light for detecting the reflectance of the sample S is obtained by introducing light from the white light source 311 into the spectroscope 313 to make monochromatic light. The monochromatic probe light irradiates the sample S via the condenser lens 314. Meanwhile, an periodic stress is applied to the sample S by the piezoelectric device 322 to modulate the light reflected from the sample S. In this state, the lock-in amplifier 137 is adjusted to be in phase so that the detection signal from the signal detector 332 is synchronized with the reference frequency signal supplied from the AC power supply 321.

The above setting is followed by acquisition of data. First, the spectroscope 313 starts scanning while the probe light reflected on the sample S is converted into the electric signal by the signal detector 332. The resultant signal is split into the DC component corresponding to the reflectance R and the AC component corresponding to the modulation reflectance $\Delta R$ through the band pass filter circuit 135. The AC component is measured by the DC voltmeter 136, while the DC component is measured by the lock-in amplifier 137. The computer 140 calculates $\Delta R/R$ using each measured value and plots it as a function of photon energy or wavelength to obtain the PZR spectrum.

Next, the PZR spectrum is measured as described above (step f1), followed by estimating the resultant spectrum amplitude of the third derivative lineshape signal or the FK oscillation profile originating from a layer of interest (step f2). The FK oscillation profile typically consists of a plurality of oscillations. For analysis, choice of an oscillation with the best signal to noise ratio is essential; namely, the largest amplitude ensures precision of values resulting from the analysis. The oscillation with the largest amplitude appears around the band gap energy of the layer of interest, therefore, it is suitable to estimate the amplitude from this oscillation. Hereinafter the amplitude of the FK oscillation profile or the third derivative lineshape signal will be simply referred to as PZR signal intensity, unless otherwise denoted.

Finally, the density of defect is obtained from the resultant PZR signal intensity (step f3). In the resultant spectrum, as described above, the amplitude of the FK oscillation profile resulting from the layer of interest depends on a state (crystallinity, etc) of the layer of interest. Then, PZR measurement of a standard sample having a known density of defect is performed in advance to prepare a conversion curve with the horizontal axis corresponding to density of defect and the vertical axis corresponding to PZR signal intensity. The density of defect can be obtained by comparing the PZR signal intensity of the sample under test with an working curve, based on the conversion curve.

Figure 20A:
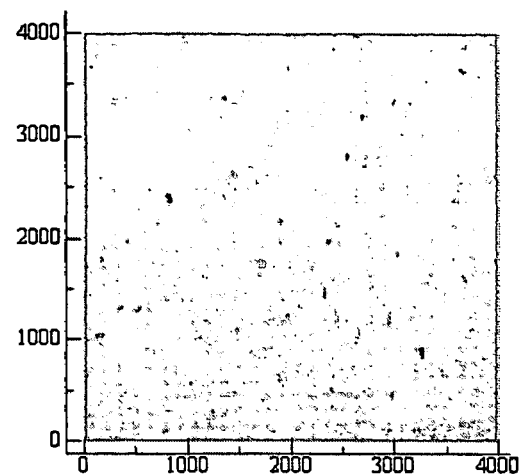
FIGS. 20A to 20C are surface AFM images resulting from observation of three samples A to C under test, each having a heterostructure of AlGaN/GaN deposited on a sapphire substrate.
Figure 20B:
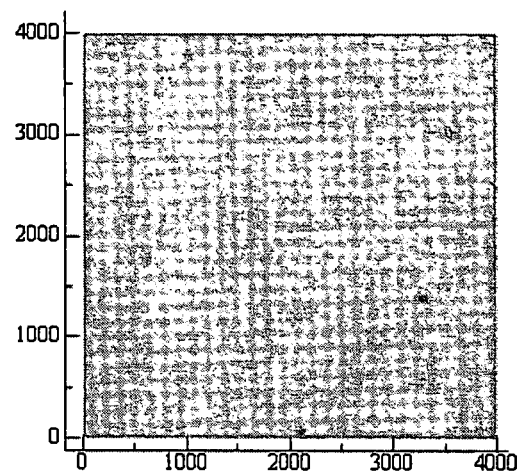
Figure 20C:
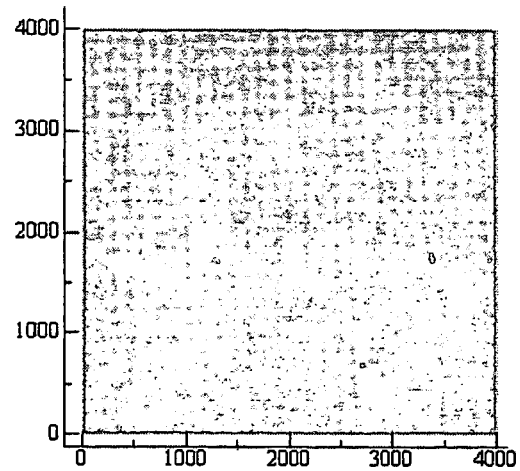

Next, applicability of the above-described modulation reflectance spectroscopy to surface morphology analysis is discussed. Herein, working examples of estimating density of defect using the PR measurements are described. FIGS. 20A to 20C show the surface AFM images resulting from observation of three samples A to C under test, each having a heterostructure of $Al_{0.2}Ga_{0.8}N$/GaN grown on a sapphire substrate, wherein all the samples have the same thicknesses of the AlGaN layer and the GaN layer.

It is apparent that the AFM image of the sample A in FIG. 20A that there are a large number of cracks on the surface of the AlGaN layer. Such cracks are little observed in FIGS. 20B and 20C corresponding to the samples B and C. But the AFM image of the sample B shows a number of pits. In general, the pits, which are accompanied by threading dislocations, are considered to be formed by trigger of impurities gathering around the threading dislocation.

Figure 21:
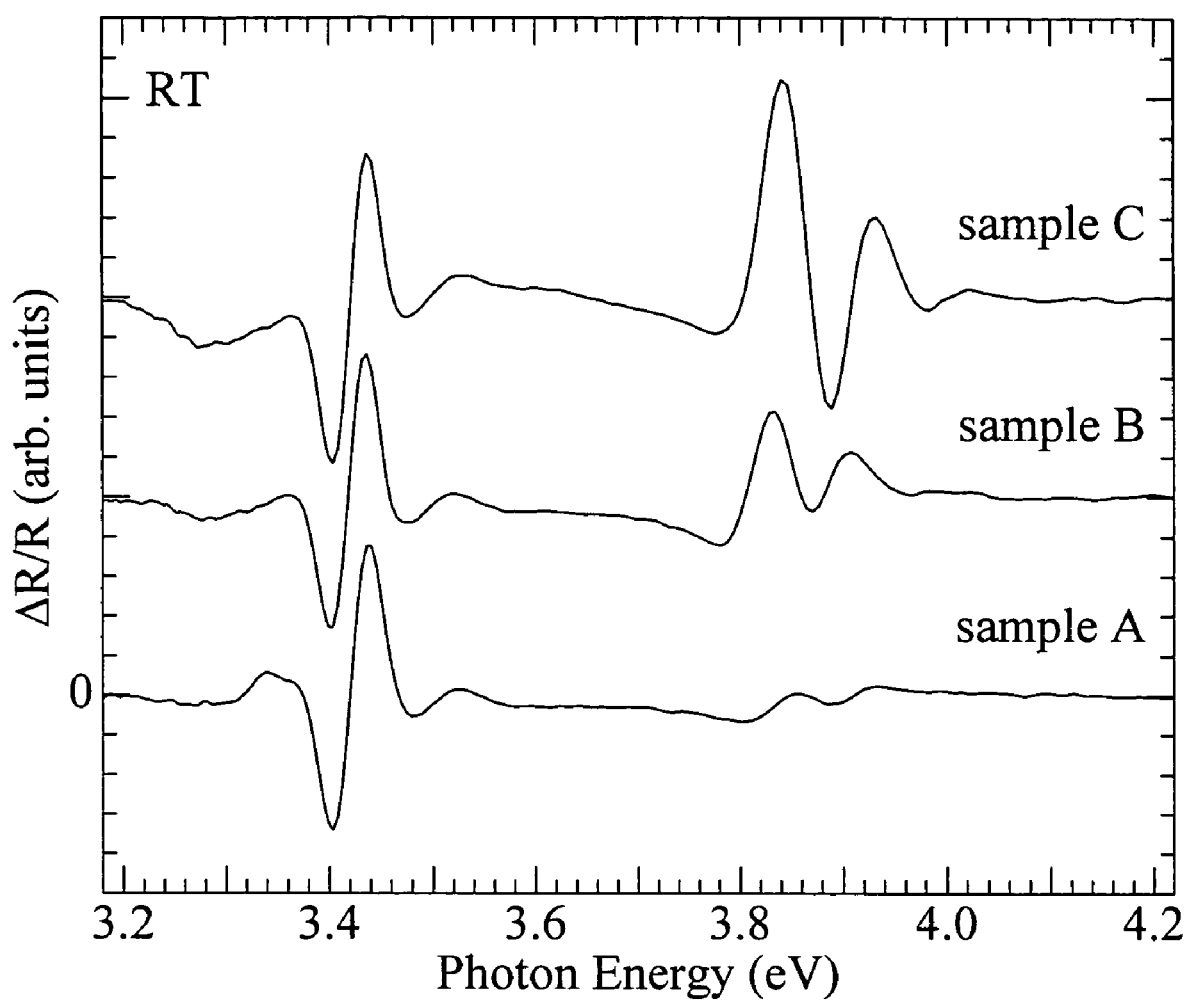
FIG. 21 shows PR spectra of the samples A to C shown in FIGS. 20A to 20C.

FIG. 21 shows the PR spectra of the samples A to C, measured at room temperature. The characteristic spectral structure around photon energy of 3.4 eV originates from the GaN layer, since the position of the spectral structure is approximately equal to the band gap energy of GaN. Hence another oscillation structure starting from photon energy of 3.8 eV results from the FK oscillations from the AlGaN layer.

Amplitude of the FK oscillation profile of the AlGaN layer is reduced in order of the samples A to C, which is in accordance with degrading of surface morphology shown in FIGS. 20A to 20C. Accordingly, it is concluded that analysis of amplitude of FK oscillation profile is applicable to a means for quantification of surface morphology.

It is apparent that the aforementioned surface morphology analysis using reflection spectroscopy shows only a little significant difference between presence and absence of pits on the surface of the AlGaN layer, whereas the surface morphology analysis based on PR spectroscopy is more sensitive than that using the ordinary reflection spectroscopic measurement. Thus, PR spectroscopic measurement of a plurality of standard samples, each having a known density of defect, is performed in advance to prepare a conversion curve, which can be obtained by plotting the intensity of the PR signal versus the density of defect, thereby obviously estimating an unknown density of defect of a sample under test based on the intensity of the PR signal thereof.

Finally, it is discussed below that the optical reflection measurement and the PR spectrum measurement, as described in the present specification, are more sensitive to surface morphology than conventional techniques for evaluating crystals.

Figure 22:
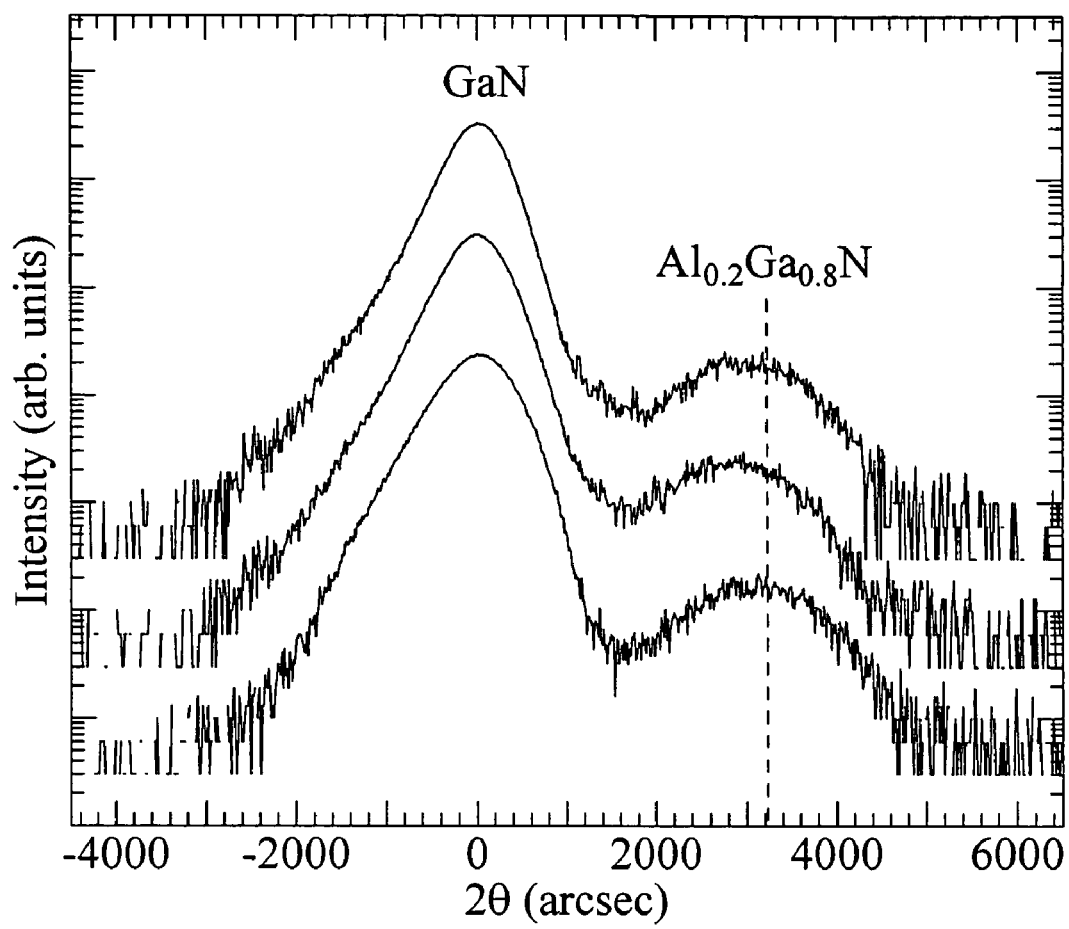
FIG. 22 shows spectra of X-ray diffraction ω-2θ of the samples A to C shown in FIGS. 20A to 20C.

FIG. 22 shows the ω-2θ X-ray diffraction patterns of the samples A to C, measured around a Bragg angle of GaN (0004) reflection. The vertical axis corresponds to intensity of X-ray diffraction (logarithmic and arbitrary unit), and the horizontal axis corresponds to diffraction angle 2θ (arcsec). The dashed line is positioned at a Bragg angle of $Al_{0.2}Ga_{0.8}N$ (0004) reflection, which is calculated on condition that the $Al_{0.2}Ga_{0.8}N$ layer is grown pseudomorphiccally on the GaN layer.

From comparing the position of the dashed line with the X-ray diffraction pattern, it is found that the peak structure around 3,100 (arcsec) results from the $Al_{0.2}Ga_{0.8}N$ (0004) reflection. Each position of the peak thereof is slightly shifted, which depends on samples. This means that each composition of the AlGaN layer is slightly different from each other. Except for the position of the peak being shifted, the shape of the X-ray diffraction pattern of the $Al_{0.2}Ga_{0.8}N$ (0004) reflection scarcely depends on the surface morphology of the AlGaN layer, unlike the reflection and the PR spectrum. This leads to a conclusion that the optical reflection measurement and the PR spectrum measurement are more suitable in evaluation of surface morphology.

Although the present invention has been fully described in connection with the preferred embodiments thereof and the accompanying drawings, it is to be noted that various changes and modifications are apparent to those skilled in the art. Such changes and modifications are to be understood as included within the scope of the present invention as defined by the appended claims unless they depart therefrom.

What is claimed is:

1. A method for evaluating semiconductor layers including:
   irradiating semiconductor layers on a substrate with light;
   measuring an optical spectrum peculiar to excitons in the semiconductor layers; and
   analyzing a broadening factor of spectral features of the optical spectrum, wherein the broadening factor is quantified by expressing a refractive index function of any surface state using a calculation model of convolution of both a refractive index function peculiar to a material and a distribution function.

2. The method for evaluating semiconductor layers according to claim 1, wherein the semiconductor layers are nitride semiconductors.

3. An apparatus for evaluating semiconductor layers, the apparatus comprising:
   a sample stage for holding a sample including semiconductor layers under test;
   a light source for irradiating the semiconductor layers with light;
   a spectrum measuring apparatus for measuring an optical spectrum peculiar to excitons in the semiconductor layers;
   a spectrum analyzing apparatus for analyzing a broadening factor of optical spectral features of the optical spectrum;
   an optical path detection apparatus for detecting deviation of the optical path of the light reflected from the sample; and
   an adjusting mechanism for adjusting position or angle of the sample stage based on the deviation of the optical path detected by the optical path detection apparatus.

4. The apparatus for evaluating semiconductor layers, according to claim 3, comprising:
   a splitting optical device for picking up a part of the light reflected from the sample; and
   an optical position detector for detecting position of the light picked up by the splitting optical device.

5. A method for evaluating semiconductor layers, including:
   irradiating semiconductor layers on a substrate with light;
   applying modulation having a predetermined frequency to the semiconductor layers to change physical characteristics of the semiconductor layers;
   detecting the light reflected from the semiconductor layers;
   extracting a component of the modulation frequency from a detected signal of the reflected light; and
   measuring an optical spectrum peculiar to excitons in the semiconductor layers while changing wavelength of the irradiating light.

6. The method for evaluating semiconductor layers according to claim 5, including, while applying the modulation to the semiconductor layers, irradiating the semiconductor layers with excitation light modulated at the predetermined frequency.

7. The method for evaluating semiconductor layers, according to claim 5, including, while applying the modulation to the semiconductor layers, applying an electric field modulated at the predetermined frequency to the semiconductor layers.

8. The method for evaluating a semiconductor layer, according to claim 5, including, while applying the modulation to the semiconductor layers, applying a stress modulated at the predetermined frequency to the semiconductor layers.

* * * * *